US009255296B2

(12) United States Patent
Al-Murrani et al.

(10) Patent No.: US 9,255,296 B2
(45) Date of Patent: Feb. 9, 2016

(54) COMPOSITIONS AND METHODS FOR DIAGNOSING AND TREATING KIDNEY DISORDERS IN A FELINE

(75) Inventors: Samer Waleed Al-Murrani, Topeka, KS (US); Xiangming Gao, Topeka, KS (US); Sukhaswami Malladi, Lawrence, KS (US)

(73) Assignee: HILL'S PET NUTRITION, INC., Topeka, KS (US)

( * ) Notice: Subject to any disclaimer, the term of this patent is extended or adjusted under 35 U.S.C. 154(b) by 0 days.

(21) Appl. No.: 13/985,917

(22) PCT Filed: Feb. 24, 2011

(86) PCT No.: PCT/US2011/026032
§ 371 (c)(1),
(2), (4) Date: Aug. 16, 2013

(87) PCT Pub. No.: WO2012/115648
PCT Pub. Date: Aug. 30, 2012

(65) Prior Publication Data
US 2013/0344196 A1      Dec. 26, 2013

(51) Int. Cl.
*C12Q 1/68* (2006.01)
*G01N 33/68* (2006.01)
*A23K 1/18* (2006.01)

(52) U.S. Cl.
CPC ............ *C12Q 1/6883* (2013.01); *A23K 1/1846* (2013.01); *G01N 33/6893* (2013.01); *C12Q 2600/112* (2013.01); *G01N 2800/347* (2013.01)

(58) Field of Classification Search
None
See application file for complete search history.

(56) References Cited

U.S. PATENT DOCUMENTS

| | | |
|---|---|---|
| 4,437,975 A | 3/1984 | Gillespie et al. |
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 4,988,617 A | 1/1991 | Landegren et al. |
| 5,143,854 A | 9/1992 | Pirrung et al. |
| 5,242,794 A | 9/1993 | Whiteley et al. |
| 5,333,675 A | 8/1994 | Mullis et al. |
| 5,409,818 A | 4/1995 | Davey et al. |
| 5,413,909 A | 5/1995 | Bassam et al. |
| 5,445,934 A | 8/1995 | Fodor et al. |
| 5,494,810 A | 2/1996 | Barany et al. |
| 5,541,061 A | 7/1996 | Fodor et al. |
| 5,547,839 A | 8/1996 | Dower et al. |
| 5,554,517 A | 9/1996 | Davey et al. |
| 5,578,832 A | 11/1996 | Trulson et al. |
| 5,631,734 A | 5/1997 | Stern et al. |
| 5,677,195 A | 10/1997 | Winkler et al. |
| 5,744,305 A | 4/1998 | Fodor et al. |
| 5,770,722 A | 6/1998 | Lockhart et al. |
| 5,800,992 A | 9/1998 | Fodor et al. |
| 5,834,758 A | 11/1998 | Trulson et al. |
| 5,856,092 A | 1/1999 | Dale et al. |
| 5,858,659 A | 1/1999 | Sapolsky et al. |
| 5,861,245 A | 1/1999 | McClelland et al. |
| 5,871,928 A | 2/1999 | Fodor et al. |
| 5,874,219 A | 2/1999 | Rava et al. |
| 5,902,723 A | 5/1999 | Dower et al. |
| 5,936,324 A | 8/1999 | Montagu |
| 5,981,956 A | 11/1999 | Stern |
| 6,013,449 A | 1/2000 | Hacia et al. |
| 6,020,135 A | 2/2000 | Levine et al. |
| 6,025,601 A | 2/2000 | Trulson et al. |
| 6,033,860 A | 3/2000 | Lockhart et al. |
| 6,040,138 A | 3/2000 | Lockhart et al. |
| 6,040,193 A | 3/2000 | Winkler et al. |
| 6,045,996 A | 4/2000 | Cronin et al. |
| 6,063,603 A | 5/2000 | Davey et al. |
| 6,090,555 A | 7/2000 | Fiekowsky et al. |
| 6,141,096 A | 10/2000 | Stern et al. |
| 6,156,501 A | 12/2000 | McGall et al. |
| 6,177,248 B1 | 1/2001 | Oliner et al. |
| 6,185,030 B1 | 2/2001 | Overbeck |
| 6,197,506 B1 | 3/2001 | Fodor et al. |
| 6,201,639 B1 | 3/2001 | Overbeck |
| 6,218,803 B1 | 4/2001 | Montagu et al. |
| 6,225,625 B1 | 5/2001 | Pirrung et al. |

(Continued)

FOREIGN PATENT DOCUMENTS

| | | |
|---|---|---|
| CN | 101336373 | 12/2008 |
| EP | 0985932 | 3/2000 |
| WO | WO 88/10315 | 12/1988 |
| WO | WO 90/06995 | 6/1990 |
| WO | WO 99/47964 | 9/1999 |
| WO | WO 01/88544 | 11/2001 |
| WO | WO 2004/005934 | 1/2004 |
| WO | WO 2006/071952 | 7/2006 |
| WO | WO 2006/119049 | 11/2006 |
| WO | WO 2011/079280 | 6/2011 |

OTHER PUBLICATIONS

Altschul et al., "Basic Local Alignment Search Tool", J. Mol. Biol., 1990, 215:403-410.
Altschul et al., "Gapped BLAST and PSI-BLAST: a new generation of protein database search programs", Nucl. Acids Research, 1997, 25(17):3389-3402.
Arata et al., "Urinary transforming growth-factor-B1 in feline chronic renal failure", J. Vet. Medical Sci., Jap. Soc. Vet. Sci., 2005, 67(12): 1253-1255.
Barringer et al., "Blunt-end and single-strand ligations by *Escherichia coli* ligase: influence on an in vitro amplification scheme," Gene, 1990, 89:117-122.

(Continued)

*Primary Examiner* — Catherine S Hibbert

(57) ABSTRACT

The present invention provides a method of diagnosing the existence of a kidney disorder in a feline comprising measuring the level of expression of one or more biomarkers selected from the group consisting of lumican; collagen alpha 1 (111) chain, variant 12; decorin; secreted frizzled-related protein 2; retinol binding protein 5; MMP-2; MMP-7; and MMP-19, in a biological sample from the feline, wherein differences in expression of the one or more biomarkers in the sample relative to a control value for expression in a sample from a normal animal indicate the existence of a kidney disorder; a method of treating a feline so diagnosed; and compositions, reagents and kits for carrying out the specified methods.

14 Claims, 16 Drawing Sheets

(56) References Cited

U.S. PATENT DOCUMENTS

| | | | |
|---|---|---|---|
| 6,284,460 B1 | 9/2001 | Fodor et al. | |
| 6,300,063 B1 | 10/2001 | Lipshutz et al. | |
| 6,300,070 B1 | 10/2001 | Boles et al. | |
| 6,309,822 B1 | 10/2001 | Fodor et al. | |
| 6,333,179 B1 | 12/2001 | Matsuzaki et al. | |
| 6,344,316 B1 | 2/2002 | Lockhart et al. | |
| 6,361,947 B1 | 3/2002 | Dong et al. | |
| 6,368,799 B1 | 4/2002 | Chee | |
| 6,386,749 B1 | 5/2002 | Watts et al. | |
| 6,391,592 B1 | 5/2002 | Su et al. | |
| 6,391,623 B1 | 5/2002 | Besemer et al. | |
| 6,410,276 B1 | 6/2002 | Burg et al. | |
| 6,582,938 B1 | 6/2003 | Su et al. | |
| 6,632,611 B2 | 10/2003 | Su et al. | |
| 6,872,529 B2 | 3/2005 | Su | |
| 6,958,225 B2 | 10/2005 | Dong | |
| 7,482,135 B2 | 1/2009 | Verheijen et al. | |
| 7,689,022 B2 | 3/2010 | Weiner et al. | |
| 2003/0073100 A1 | 4/2003 | Cate et al. | |
| 2004/0038856 A1 | 2/2004 | Chakravarty et al. | |
| 2004/0101924 A1 | 5/2004 | Diamant et al. | |
| 2005/0032063 A1 | 2/2005 | Kopreski | |
| 2005/0124534 A1 | 6/2005 | Noble et al. | |
| 2006/0094863 A1 | 5/2006 | Yamashita et al. | |
| 2006/0200320 A1* | 9/2006 | Al-Murrani | 702/20 |
| 2007/0015227 A1 | 1/2007 | Moses et al. | |
| 2007/0065816 A1 | 3/2007 | Dong et al. | |
| 2007/0118295 A1* | 5/2007 | Al-Murrani | 702/19 |
| 2007/0184439 A1 | 8/2007 | Guilford et al. | |
| 2007/0243214 A1 | 10/2007 | Schiemann et al. | |
| 2007/0254290 A1 | 11/2007 | Yen et al. | |
| 2009/0117604 A1 | 5/2009 | Verheijen et al. | |
| 2011/0229895 A1* | 9/2011 | Walz | 435/6.12 |
| 2012/0220488 A1* | 8/2012 | Li | 506/9 |
| 2012/0283123 A1* | 11/2012 | Sarwal | C12Q 1/6883 506/9 |

OTHER PUBLICATIONS

U.S. Appl. No. 09/916,135, filed Jul. 25, 2001.
Dong et al., "Flexible use of high-density oligonucleotide arrays for single-nucleotide polymorphism discovery and validation", Genome Research, 2001, 11:1418.
Eckert et al., "DNA Polymerase fidelity and the polymerase chain reaction", PCR Methods and Applications, 1991, 1:17-24.
Esteve et al., "The advantages and disadvantages of Sfrp1 and Sfrp2 Expression in pathological events", 2010, Tohoku J. Exp. Med. 221(1):11-17.
Fan et al., "A class of models for analyzing GeneChip gene expression analysis array data", BMC Genomics, 2005, 6:16.
Folli et al., "Identification, retinoid binding, and x-ray analysis of a human retinol-binding protein", PNAS, 2001, 98(7):3710-3715.
Folli et al., "The status, quality, and expansion of the NIH full-lengthcDNA project: The Mammalian Gene Collection (MGC)", Genome Research, 2004, 14:2121-2127.
Forterre et al., "Protein profiling of urine from dogs with renal disease using ProteinChip analysis", 2004, J. Vet. Diag. Invest. 16(4):271-277.
Frey et al., "Isoforms of Retinol binding protein 4 (RBP4) are increased in chronic diseases of the kidney but not of the liver", Lipids in Health and Disease, 2008, 7:29.
Guatelli et al., "Isothermal, in vitro amplification of nucleic acids by a multienzyme reaction modeled after retroviral replication", 1990, PNAS 87:1874-1878.
Hein et al., "BGX: a fully Bayesian integrated approach to the analysis of Affymetrix GeneChip data", 2005, Biostatistics 6:349-373.
Ho et al., "Down-regulation of retinol binding protein 5 is associated with aggressive tumor features in hepatocellular carcinoma", J. Cancer Research Clin. Oncol., 2007, 133:929-936.
International Search Report and Written Opinion issued in PCT Application No. PCT/US2011/026032 on Mar. 16, 2012.
Irizarry et al., "Exploration, normalization, and summaries of high density oligonucleotide array probe level data", 2003, Biostatistics 4:249-264.
Irizarry et al., "Summaries of affymetrix GeneChip probe level data", Nucleic Acid Research, 2003, 31(4): e15.
Karlin et al., "Methods for assessing the statistical significance of molecular sequence features by using general scoring schemes", 1990, PNAS 87:2264-2268.
Kwoh et al., "Transcription-based amplification system and detection of amplified human immunodeficiency virus type 1 with a bead-based sandwich hybridization format", 1989, PNAS 86:1173.
Landegren et al., "A ligase-mediated gene detection technique", Science, 1988, 241:1077.
Lapointe et al., "N-Acetyl-B-D-Glucosaminidase index as an early biomarker for chronic kidney disease in cats with hyperthyroidism", J.Vet. Intern.. Med., 2008, 22(5): 1103-1110.
Lenz et al., "Glomerular endothelial cells synthesize collagens but little gelatinase A and B", J. Amer. Soc. Nephrol., 1998, 9:2040-2047.
Lenz et al., "Matrix metalloproteinases in renal development and disease", J. Amer. Soc. Nephrol., 2000, 11:574-581.
Li et al., "Model-based analysis of oligonucleotide arrays: expression index computation and outlier detection", 2001, Proc. Acad. Sci. 98:31-36.
Mattila et al., "Fidelity of DNS synthesis by the Thermococcus litoralis DNA polymerase—an extremely heat stable enzyme with proofreading activity", Nucleic Acids Research, 1991, 19(18):4967-4973.
Nagase et al., "Matrix metalloproteinases", J. Biol. Chem., 1999, 274(31):21491-21494.
Nielson et al., "Sequence-selective recognition of DNA by strand displacement with a thymine-substituted polyamide", Science, 1991, 254:1497-1500.
Nielson, "Applications of peptide nucleic acids", 1999, Curr. Opin. Biotechnol. 10:71-75.
Paciello et al., "Decorin and lumican are differentially expressed in canine masticatory muscle myositis", 2008, Neuromuscular Disorders, 18:724-725.
Piantedosi et al.,"Cellular retinol-binding protein type III is needed for retinoid incorporation into milk", 2005, J. Biol. Chem. 280(25): 24286-24292.
Polzin et al., "Dietary management of feline chronic renal failure:where are we now? In what direction are we headed?", J. Feline Med. Surgery, 2000, 2:75-82.
Raila et al., "The distribution of v+C27itamin A and retinol-binding protein in the blood plasma, urine, liver and kidneys of carnivores," 2000, Vet. Res. 31:541-551.
Raila et al., 2001, Berl. Munich Tierarzh Wochenschr. 114(7-8):257-266.
Raila, "Immunochemical localization of megalin, retinol-binding protein and Tamm-Horsfall glycoprotein in the kidneys of dogs", 2003, Vet. Res. Commun. 27(2):125-135.
Sanders et al., "Renal expression of matrix metalloproteinases in human ANCA-associated glomerulonephritis", 2004, Nephrol. Dial. Transplant 19:1412-1419.
Sato et al., "Roles of membrane-type matrix metalloproteinase-1 in tumor invasion and metastasis", 2005, Cancer Sci. 96:212-217.
Schaefer et al The FASEB J express article:Small proteoglycans in human diabetic nephropathy: discrepancy between glomerular expression and protein accumulation of decorin, biglycan, lumican, and fibromodulin, pub online Jan. 19, 2001. FASEB J. 10.1096/fj.00-493fje. (online).
Schaefer et al., "Small proteoglycans of normal adult human kidney: distinct expression patters of decorin, biglycan, fibromodulin, and lumican", 2000, Kidney Int. 58:1557-1568.
Schwab et al., "Microarray analysis of focal segmental glomerulosclerosis", 2004, Amer. J. Nephrol. 24:438-447.
Van Hoek et al., "Immunoassay of urinary retinol binding protein as a putative renal marker in cats", 2007, J. Immunol. Meth. 329 (1-2): 208-213.
Van Hoek et al., "Immunoassay of urinary retinol binding protein as a putative renal marker in cats", J. Immunological Methods 2008, 329:208-213.
Van Hoek et al., "Retinol-binding protein in serum and urine of hyperthyroid cats before and after treatment with radioiodine", J.Vet. Intern. Med., 2009, 23(5): 1031-1037.

(56) References Cited

OTHER PUBLICATIONS

Werten et al., "Gecko i-crystallin: how cellular retinol-binding protein became an eye lens ultraviolet filter", 2000, PNAS 97:3282-3287.
Written Opinion issued in PCT Application No. PCT/US11/26032 on May 28, 2013.
Wu et al., "The litigation amplification reaction (LAR)—amplification of specific DNA sequences using sequential rounds of template dependent ligation", 1989, Genomics 4:560-569.
Yamamura et al., Oncogenic functions of secreted frizzled-related protein 2 in human renal cancer, Mol. Cancer Ther., 2010, 9(6):1680-1687.
Yeh, "Soluble lumican glycoprotein purified from human amniotic membrane promotes corneal epithelial wound healing", Investigative Opthalmol. Visual Sci., 2005, 46(2):479-486.
Young et al., "Efficient isolation of genes by using antibody probes", 1983, PNAS 80:1194-1198.
Zhou et al., "An expression index for Affymetrix GeneChips based on the generalized logarithm", 2005, Bioinformat. 21(21): 3983-3989.
Abrass CK, Alterations in chromatin are associated with increases in collagen III expression in aging nephropathy, Am J Physiol Renal Physiol. Feb. 2011; 300(2), abstract.
Hoshi, "Diagnosis of Renal Impairment by Urinary Trace Protein Analysis in Cats," Journal of Veterinary Medicine, 2004; 57(1): 46-51.
Kuroda M, Glomerular expression of biglycan and decorin and urinary levels of decorin in primary glomerular disease,. Clin Nephrol. Jan. 2004; 61 {1):7-16, abstract.
Miyata Y, Expression of matrix metalloproteinase-7 on cancer cells and tissue endothelial cells in renal cell carcinoma: prognostic implications and clinical significance for invasion and metastasis. Clin Cancer Res. Dec. 1, 2006; 12(23), abstract.
The Meeting of the Japanese Society of Veterinary Science (Abstract), 2004; 132: 139.
Urakami S, Wnt antagonist family genes as biomarkers for diagnosis, staging, and prognosis of renal cell carcinoma using tumor and serum DNA., Clin Cancer Res. Dec. 1, 2006; 12{23), abstract.
Yang SD, The expression and clinical significance of TGF-beta 1 and MMP2 in human renal clear cell carcinoma, Int J Surg Pathol. Apr. 2010; 18(2), abstract.

* cited by examiner

COMPOSITIONS AND METHODS FOR DIAGNOSING AND TREATING KIDNEY DISORDERS IN A FELINE

CROSS-REFERENCE TO RELATED APPLICATIONS

This application is a U.S. National Stage Entry under 35 U.S.C. §371 of International Patent Application No. PCT/US2011/026032, filed Feb. 24, 2011, (now expired).

FIELD OF THE INVENTION

The present invention relates to compositions, materials and methods for diagnosing and/or monitoring kidney diseases and disorders in felines, including methods for: diagnosing of, devising and monitoring a treatment plan for, and monitoring the status of, a kidney disorder characterized by an abnormal loss of renal function, renal failure, reduced glomerular filtration rate or glomerulonephritis, in a feline, by measuring expression of selected genes.

SEQUENCE LISTING

The instant application contains a Sequence Listing which has been submitted via EFS-Web and is hereby incorporated by reference in its entirety. Said ASCII copy, created on Mar. 30, 2010, is named 8888P0US.txt and is 7,809 bytes in size.

BACKGROUND OF THE INVENTION

Nephritis is a general term for inflammation of the kidney, which may be a focal or diffuse proliferative or destructive disease involving the glomerulus, renal tubule or the kidney interstitial (or connective) tissue. Nephritis may progress through a number of stages ending in end-stage kidney disease or end-stage renal failure. The most common form of nephritis is glomerulonephritis.

Glomerulonephritis or glomerular nephritis ("GN") is a condition characterized by inflammation of the glomeruli or capillary loops of the kidney. The condition occurs in acute, sub-acute and chronic forms and may be idiopathic, or secondary to an infection, disease or exposure to a toxin.

Renal failure is the inability of the kidney to maintain its normal functions. As a result, metabolic waste products and metabolites accumulate in the blood. These waste products and metabolites may adversely affect most bodily systems. Disturbances in the maintenance of fluid and electrolyte balances are characteristic of renal failure.

Acute renal failure may occur suddenly due to trauma, infection, inflammation or exposure to nephrotoxic substances. This condition may result in dehydration, hypotension and circulatory collapse. Acute renal failure is frequently segregated into three categories: (1) pre-renal failure, which is associated with decreased renal blood flow; (2) intra-renal failure, which is associated with ischemia and toxins; and (3) post-renal failure, which results from obstruction of urine flow.

Chronic renal failure involves a progressive loss of kidney function that may eventually progress to end-stage renal disease or failure. At inception, chronic renal failure begins as a diminishing kidney function, without appreciable accumulation of metabolic waste products in the blood. As the glomerular filtration rate slows due to inflammation, waste products begin to accumulate. The disease progresses to uremia due to low kidney function, and high levels of protein end products start to accumulate and impair bodily functions. Common causes of chronic renal failure include: inflammation, infection, urinary tract obstruction and certain systemic diseases and toxicities, including hypercalcemia, lupus erythematosus, diabetes mellitus and hypertension.

End-stage renal disease is marked by irreversible chronic renal failure. Serum creatinine and blood urea nitrogen levels continue to rise and the resulting uremia impairs all bodily systems. The kidney can suffer permanent and almost complete loss of function, on the order of 10% or less of normal kidney function. One cause of end-stage kidney disease is glomerulonephritis. Other causes include those mentioned for chronic renal failure.

Glomeruli are one of the structural components of the nephron of the kidney and are composed of small blood vessels frequently described as a capillary tuft or cluster. The nephron is the basic structural and functional unit of the kidney, which is also comprised of a structure known as a malpighian, or Bowman's, capsule, as well as comprising arterioles and tubules. Bowman's capsule contains the glomeruli loops and the renal tubule. Glomeruli are very small capillaries, hence the blood flow through these vessels is very slow and molecules in the blood can become easily deposited on the walls of these tiny capillaries. Renal tubules are comprised of a basement membrane and epithelial lining and serve to secrete, collect and conduct urine.

The glomerulus functions as a filter within the nephron. Water and small molecules in the blood flow through the glomerulus and are filtered through a structure referred to as the basement membrane, which is formed by the glomerulus and Bowman's capsule. The filtrate comprising water and small molecules passes through the renal tubule to be absorbed and reabsorbed before finally being converted to urine. The basement membrane is comprised of pores of various sizes which serve to filter small molecules and to prevent the passage through the basement membrane of larger molecules. The specific function of the nephron is to remove from the plasma certain end products of metabolism such as uric acid, urea and creatinine as well as excess electrolytes, e.g. sodium, chloride and potassium ions. By reabsorbing water and electrolytes, the nephron plays an important role in maintaining normal fluid balance in the body.

Creatinine is a nitrogenous compound formed as a result of creatine metabolism. Creatine, in turn, is a non-proteinaceous substance that is synthesized in the body from three amino acids, arginine, glycine and methionine. The molecule is found in muscle in small amounts and, when combined with phosphate as phosphocreatine, serves as a storage form of high energy phosphate used in various metabolic processes. Creatinine is absorbed into the blood and ultimately is excreted in the urine. Thus, a simple laboratory test for measuring creatinine in the blood can be used to determine kidney function. The test is frequently referred to as a creatinine clearance test, which measures the amount of creatinine cleared from plasma in a given time interval. Because creatinine is formed from phosphocreatine in relatively constant amounts, a rise in creatinine levels in the blood is indicative of a kidney malfunction, i.e., loss of kidney function.

Glomerulonephritis may arise as a result of a biological insult to the immune system. Foreign substances may adhere to the basement membrane and cause an immune response resulting in the production of antibodies. These antibodies may combine with the foreign substances to cause immune complexes that become deposited on the walls of the tiny glomerular capillaries, resulting in damage to the nephron. Alternatively, in some individuals the immune system can create autoantibodies which are immunoglobulins that may attack kidney cells resulting in a so-called autoimmune response. If proteins in the body are altered, an autoantibody response may ensue because the autoantibodies recognize the altered proteins as non-self. These autoantibody-protein complexes may likewise be deposited on the basement membrane of the glomerulus causing a disruption of the functioning of the nephron.

Glomerulonephritis is a common cause of proteinuria in felines and may be either the idiopathic or secondary form of the condition. In the latter situation, the condition may develop secondary to neoplasia, inflammatory diseases, endocrine malfunctions, infections or familial nephropathies. As in humans, glomerulonephritis in felines is often mediated immunologically, involving immunoglobulins and complement factors in the body of the animal. Injury occurs within the glomeruli of the kidney resulting in morphological changes to the glomeruli. Eventually the injury is irreversible and leads to malfunction of the nephrons.

Glomerulonephritis is characterized in the scientific literature in a number of different forms based on the histopathological changes taking place. Membranous glomerulonephritis involves thickening of the glomerular basement membrane. Proliferative or mesangioproliferative glomerulonephritis is characterized by proliferation of cells in the mesangial matrix. Membranoproliferative glomerulonephritis involves a combination of the foregoing changes. Glomerulosclerosis is characterized by increased matrix formation and scarring. In some cases there are minimal changes to the glomeruli and only slight increases in mesangial cell proliferation.

A number of methods have been developed for studying differential gene expression, e.g., DNA microarrays, expressed tag sequencing (EST), serial analysis of gene expression (SAGE), subtractive hybridization, subtractive cloning and differential display (DD) for mRNA, RNA-arbitrarily primed PCR (RAP-PCR), real-time PCR (RT-PCR), representational difference analysis (RDA), two-dimensional gel electrophoresis, mass spectrometry, and protein microarray based antibody-binding for proteins.

Due to the complexity of the biological pathways implicated in renal disease and the inherent molecular interactions and intercellular signaling processes, it is highly desirable to understand at a genetic level the interactions that are taking place. Detection of dysregulated genes in the early stages of loss of renal function in felines is helpful in understanding the biology of renal disease, especially glomerulonephritis on a genome-wide basis. The fact that gene dysregulation may be detected at an early stage of disease development in animals subjected to repeated ischemic injury is helpful in designing methods for diagnosing of, and devising and monitoring a treatment plan for, an abnormal loss of kidney function, renal failure, reduced glomerular filtration rate or glomerulonephritis, in a feline.

A more detailed understanding of the biological pathways involved through gene expression profiling will aid in the development of diagnostic procedures, reagents and test kits as well as salutary pharmaceutical, nutraceutical and nutritional (dietary) interventions in the disease pathways. These approaches may enable early detection and potentially prevention or treatment of the underlying kidney disorder, particularly glomerulonephritis, as well as in monitoring the prognosis of early stage renal failure and glomerulonephritis, especially in felines. Dysregulated genes involved in the pathology of such disorders may serve as important biomarkers for diagnosis and potentially prevention or treatment of the disorder and to optimize selection of appropriate pharmaceutical, nutraceutical and nutritional (dietary) interventions.

The level of gene expression and/or the determination of the level of functioning of an expressed gene product in a feline may be used to select an appropriate agent for therapeutic or prophylactic use. This data may be employed by the skilled worker in selecting appropriate drugs as agents for the prevention or treatment of renal diseases in felines through gene expression profiling. Gene expression data and analysis may also be used to select nutritional compositions, dietary supplements, and nutraceuticals having a salutary effect on kidney performance by utilizing biomarkers indicative of a healthy state of kidney functioning.

Only very limited work has been done to date in screening the feline genome for gene expression profiles in connection with the diagnosis of diseases in felines. Studies in healthy populations of felines versus populations having a disease such as kidney disease and loss of kidney function as described in this specification have not been extensively conducted. Little data is available with respect to the expression profile of the feline genome, especially with respect to the development of renal diseases in felines over time.

Kidney failure is a leading cause of death in felines. To effectively treat kidney disease, it is important to address the problem early, before the kidney is seriously damaged. By the time the subject is showing signs of kidney failure, the damage may well be irreversible. This presents a challenge, because kidney disease in its early stages may not have any overt symptoms. Accordingly, there is a need for better methods to identify animals in the early stage of kidney disease, so that they can be treated appropriately, for example by giving them appropriate diets in the case of idiopathic conditions, and/or treating conditions such as infection or autoimmune disease which may be contributing to the problem in order to help reverse or at least delay and inhibit the progression of the condition.

SUMMARY OF THE INVENTION

The present invention relates to compositions and methods for: diagnosing of, devising and monitoring a treatment plan for, and monitoring the status of a kidney disorder characterized by an abnormal loss of renal function, renal failure, reduced glomerular filtration rate or glomerulonephritis, in a feline, wherein the kidney disorder is detectable by utilizing at least one relevant biomarker isolated and measured from a biological test sample taken from such feline, wherein the expression of the biomarker correlates positively or negatively with the disease. A relevant biomarker for practice of the compositions and methods of the present invention comprises a polynucleotide or protein present in such biological test sample of such feline. A biological test sample for the practice of the method of the invention may comprise, for example, a tissue sample of a kidney of such feline. The biomarkers were selected also on the basis of being secreted, so they can be detected in blood serum or plasma, or in urine. Accordingly the biological test sample may also be a specimen of a biological fluid taken from such feline, for example blood or urine.

The invention is based, in part, on the discovery that particular gene expression profiles in felines correlate with a change in such animal from a normal to an abnormal biological process in the kidney that may lead to a decline in renal function over time. A correlation of a particular gene expression profile with a decline in renal function can be predicted, detected and diagnosed in a feline without rendering a conventional clinical diagnosis based on art-recognized clinical signs and symptoms of renal disease. An altered gene expression profile in a feline is, therefore, predictive of a decline in renal function, as might otherwise be diagnosed at a later time by art-recognized measurements of renal function. Such art-recognized measurements of renal function typically may include, for example, one of the following measurements: glomerular filtration rate, creatinine clearance rate, urinary protein levels, serum creatinine levels, urinary creatinine levels, blood urea nitrogen (BUN) levels, radioisotope metabolic labeling, soft tissue imaging, including sonography, magnetic resonance imaging and/or computed tomography. Non-intrusive assays such as serum creatinine and BUN levels typically show poor correlation with kidney histopathology and generally would not be predictive of future changes in the kidney.

The invention provides, for example, methods of measuring existence of a kidney disorder characterized by an abnormal loss of renal function, renal failure, reduced glomerular filtration rate or glomerulonephritis, involve evaluating the gene expression level or activity of at least one homologous feline gene or the translation product of such gene selected from the group consisting of: secreted frizzle-related protein-2 (SFRP2); retinol binding protein 5 (rbp5); lumican (LUM); decorin (DCN); collagen alpha 1 (III) chain, variant 12 (COL3A1); and matrix metalloproteinase-2, -7 and -19 (MMP2, MMP7 and MMP19).

The invention provides, for example, methods of measuring existence of a kidney disorder characterized by an abnormal loss of renal function, renal failure, reduced glomerular filtration rate or glomerulonephritis, involve evaluating the gene expression level or activity of at least one homologous feline gene or the translation product of such gene selected from the group consisting of: secreted frizzle-related protein-2 (SFRP2) and retinol binding protein 5 (rbp5); and, optionally, a second group of at least one homologous feline gene or the translation product of such gene selected from the group consisting of: lumican (LUM); decorin (DCN); collagen alpha 1 (III) chain, variant 12 (COL3A1); and matrix metalloproteinase-2, -7 and -19 (MMP2, MMP7 and MMP19).

In one embodiment, the present invention encompasses one or more genes or gene segments ("genes" as defined herein) that are differentially expressed in abnormal animals compared to normal animals. The invention is based upon the discovery of polynucleotides that are differentially expressed in abnormal animals compared to normal animals. The genes were identified by comparing the expression of genes in tissue samples taken from animals diagnosed as abnormal with genes in tissue samples from animals diagnosed as normal using Affymetrix GeneChip® technology.

The polynucleotides and genes are identified by measuring differences in gene expression from tissue samples taken from felines diagnosed as abnormal and having a kidney disorder with gene expression in tissue samples from felines diagnosed as normal. Changes in gene expression can be determined by any method known to skilled artisans. Generally, changes in gene expression are determined by measuring transcription (determining the amount of mRNA produced by a gene) or measuring translation (determining the amount of protein produced by a gene). The amount of RNA or protein produced by a gene can be determined using any method known to skilled artisans for quantifying polynucleotides and proteins.

Generally, mRNA expression is determined using polymerase chain reaction (PCR) (including, without limitation, reverse transcription-PCR (RT-PCR) and quantitative real-time PCR (qPCR)), short or long oligonucleotide arrays, cDNA arrays, EST sequencing, Northern blotting, SAGE, MPSS, MS, bead arrays and other hybridization methods. The RNA measured is typically in the form of mRNA or reverse transcribed mRNA.

Protein or polypeptide expression is determined using various colormetric and spectroscopic assays and methods such as quantitative Western blots, ELISA, 2D-gels, gas or liquid chromatography, mass-spec, the lowry assay, the biuret assay, fluorescence assays, turbidimetric methods, the bicinchoninic assay, protein chip technology, infrared absorbance, ninhydrin, the Bradford assay, and ultraviolet absorbance.

Gene chips allow a large-scale study of biological processes and the measurement of activity within a cell at a certain point in time. Microarray analysis permits one to account for differences in phenotypes on a large-scale genetic basis. Actual measurement of gene expression products is a more accurate indicator of gene function than determining sequences per se. Microarray analysis is based upon quantifying the concentration of a gene's mRNA transcript in a cell at a given time. DNA is immobilized on a medium and labeled target mRNA is hybridized with probes on the array. Binding of the labeled mRNA to the probes is measured by laser analysis. The measurement is a count of photons emitted. The entire chip is scanned and digitally imaged. The image is processed to locate probes and to assign intensity measurements to each probe. In this manner up- and down-regulated genes may be determined. The analysis enables the skilled person to find groups of genes with similar expression profiles and to determine tissues with similar expression profiles. In this manner, genes that explain the observed differences in tissue samples can be identified.

Affymetrix Gene Chips typically employ probes of 25 bp and probe sets of 11 to 20 probes corresponding to a particular gene or EST. The chip is constructed with a perfect match and mismatch probe of 25 bp each, the former being perfectly complementary to a specific region of a gene and the latter having the $13^{th}$ bp substituted to make a mismatch. A probe summarization algorithm is used to determine background correction, normalization and probe summarization, which is the conversion of probe values to probe set expression values. RMA is one of the algorithms that may be used for this purpose. The algorithm performs the last two steps of analysis, normalization and summarization of probe-level intensity measurements. The perfect match values are, therefore, background corrected, normalized and summarized into a set of expression measurements.

The raw data is analyzed using GeneSpring version 7.0 (GS) software (Agilent Corporation) and validated using the R-Bioconductor (RB) freeware. Both software packages are used to compute probe intensities from the CEL files generated by the Affymetrix Instrument. The Present/Absent/Marginal calls per probe and P-values are computed using the R-Bioconductor and GeneSpring software separately.

Generally, differential gene expression in abnormal animals compared to normal animals is determined by measuring the expression of at least one gene. Preferably, the expression of two or more differentially expressed genes is measured to provide a gene expression pattern or gene expression profile. More preferably, the expression of a plurality of differentially expressed genes is measured to provide additional information for a more significant gene expression pattern or profile.

The present invention provides a plurality of markers that together or alone are or can be used as markers of renal disease. In especially useful embodiments of the invention, a plurality of these markers can be selected and their mRNA expression may be measured simultaneously to provide expression profiles for use in various aspects of the inventions described in this application. In a preferred embodiment of the present methods and compositions, at least 2, 3, 4, 5, 6, 7 or 8 markers are selected from the group consisting of: secreted frizzle-related protein-2 (SFRP2) or a feline homolog or fragment thereof (SEQ ID NO. 9); retinol binding protein 5 (rbp5) or a feline homolog or fragment thereof (SEQ ID No.: 10); lumican (LUM) or a feline homolog or fragment thereof (SEQ ID No.: 11); decorin (DCN) or a feline homolog or fragment thereof (SEQ ID No.: 12); collagen alpha 1 (III) chain, variant 12 (COL3A1) or a feline homolog or fragment thereof (SEQ ID No.: 13); matrix metalloproteinase-2 (MMP2) or a feline homolog or fragment thereof (SEQ ID No.: 14); matrix metalloproteinase-7 (MMP7, PUMP-1) or a feline homolog or fragment thereof (SEQ ID No.: 15); and matrix metalloproteinase-19 (MMP19) or a feline homolog or fragment thereof (SEQ ID No.: 16) and can be used for determination of gene expression profiles employed in the practice of the methods of the invention. Each marker can be particularly linked to certain aspects of kidney disease.

The present invention provides a plurality of markers that together or alone are or can be used as markers of renal disease. In another especially useful embodiment of the invention, a plurality of these markers can be selected and their mRNA expression may be measured simultaneously to provide expression profiles for use in various aspects of the inventions described in this application. In a preferred embodiment of the present methods and compositions, at least 2, 3, 4, 5, 6, 7 or 8 markers are selected from the group consisting of: secreted frizzle-related protein-2 (SFRP2) or a feline homolog or fragment thereof (SEQ ID NO. 9) and retinol binding protein 5 (rbp5) or a feline homolog or fragment thereof (SEQ ID No.: 10); and, optionally, a second group of at least one polynucleotide selected from the group consisting of: lumican (LUM) or a feline homolog or fragment thereof (SEQ ID No.: 11); decorin (DCN) or a feline homolog or fragment thereof (SEQ ID No.: 12); collagen alpha 1 (III) chain, variant 12 (COL3A1) or a feline homolog or fragment thereof (SEQ ID No.: 13); matrix metalloproteinase-2 (MMP2) or a feline homolog or fragment thereof (SEQ ID No.: 14); matrix metalloproteinase-7 (MMP7, PUMP-1) or a feline homolog or fragment thereof (SEQ ID No.: 15); and matrix metalloproteinase-19 (MMP19) or a feline homolog or fragment thereof (SEQ ID No.: 16) and can be used for determination of gene expression profiles employed in the practice of the methods of the invention. Each marker can be particularly linked to certain aspects of kidney disease.

In another aspect, the invention provides a device suitable for detecting the expression of a plurality of genes differentially expressed in abnormal felines compared to normal felines. The device comprises a substrate having a plurality of the oligonucleotide or polynucleotide probes of the present invention affixed to the substrate at known locations. The device is essentially an immobilized version of the oligonucleotide or polynucleotide probes described herein. The device is useful for rapid and specific detection of genes and polynucleotides and their expression patterns and profiles. Typically, such probes are linked to a substrate or similar solid support and a sample containing one or more polynucleotides (e.g., a gene, a PCR product, a ligase chain reaction (LCR) product, a DNA sequence that has been synthesized using amplification techniques, or a mixture thereof) is exposed to the probes such that the sample polynucleotide(s) can hybridize to the probes. The probes, the sample polynucleotide(s), or both, are labeled, typically with a fluorophore or other tag such as streptavidin, and detected using methods known to skilled artisans. If the sample polynucleotide(s) is labeled, hybridization may be detected by detecting bound fluorescence. If the probes are labeled, hybridization is typically detected by label quenching. If both the probe and the sample polynucleotide(s) are labeled, hybridization is typically detected by monitoring a color shift resulting from proximity of the two bound labels. A variety of labeling strategies and labels are known to skilled artisans, particularly for fluorescent labels. Preferably, the probes are immobilized on substrates suitable for forming an array (known by several names including DNA microarray, gene chip, biochip, DNA chip, and gene array) comparable to those known in the art.

Methods for determining the amount or concentration of protein in a sample are known to skilled artisans. Such methods include radioimmunoassays, competitive-binding assays, Western blot analysis, and ELISA assays. For methods that use antibodies, polyclonal and monoclonal antibodies are suitable. Such antibodies may be immunologically specific for a protein, protein epitope, or protein fragment.

Some embodiments of the invention utilize antibodies for the detection and quantification of proteins produced by expression of the polynucleotides of the present invention. Although proteins may be detected by immunoprecipitation, affinity separation, Western blot analysis, protein arrays, and the like, a preferred method utilizes ELISA technology wherein the antibody is immobilized on a solid support and a target protein or peptide is exposed to the immobilized antibody. Either the probe, or the target, or both, can be labeled using known methods.

In a further aspect, the invention provides a method for detecting the differential expression of one or more genes differentially expressed in abnormal felines compared to normal felines in a sample. The method comprises (a) hybridizing a combination comprising a plurality of polynucleotide probes that are differentially expressed in abnormal felines compared to normal felines with polynucleotides in the sample to form one or more hybridization complexes; (b) optionally, hybridizing a combination comprising a plurality of polynucleotide probes that are differentially expressed in abnormal felines compared to normal felines with polynucleotides in a standard to form one or more hybridization complexes; (c) detecting the hybridization complexes from the sample and, optionally, the standard from step (b); and (d) comparing the hybridization complexes from the sample with the hybridization complexes from a standard, wherein a difference in the amount of hybridization complexes between the standard and sample indicate differential expression of genes differentially expressed in abnormal animals compared to normal animals in the sample.

Step (b) and part of step (c) are optional and are used if a relatively contemporaneous comparison of two or more test systems is to be conducted. However, in a preferred embodiment, the standard used for comparison is based upon data previously obtained using the method.

These probes are exposed to a sample to form hybridization complexes that are detected and compared with those of a standard. The differences between the hybridization complexes from the sample and standard indicate differential expression of polynucleotides and therefore genes differentially expressed in abnormal felines compared to normal felines in the sample. In a preferred embodiment, probes are made to specifically detect polynucleotides or fragments thereof produced by one or more of the genes or gene fragments identified by the present invention. Methods for detecting hybridization complexes are known to skilled artisans.

In another aspect, the invention provides a method for detecting the differential expression of genes differentially expressed in abnormal felines compared to normal felines in a sample. The method comprises (a) reacting a combination comprising a plurality of polypeptide probes with proteins in the sample under conditions that allow specific binding between the probes and the proteins to occur, wherein the proteins bound by the probes are differentially expressed in an abnormal feline compared to a normal feline; (b) optionally, reacting a combination comprising a plurality of polypeptide probes with proteins in a standard under conditions that allow specific binding between the probes and the proteins to occur, wherein the proteins bound by the probes are differentially expressed in an abnormal feline compared to a normal feline; (c) detecting specific binding in the sample and, optionally, the standard from step (b); and (d) comparing the specific binding in the sample with that of a standard, wherein differences between the specific binding in the standard and the sample indicate differential expression of genes differentially expressed in abnormal felines compared to normal felines in the sample.

These probes are exposed to a sample to form specific binding that is detected and compared with those of a standard. The differences between the specific binding from the sample and standard indicate differential expression of proteins and therefore genes differentially expressed in abnormal felines compared to normal felines, particularly abnormal-associated genes, in the sample. In a preferred embodiment, probes are made to specifically detect proteins or fragments thereof produced by one or more of the genes or gene fragments identified by the present invention.

In one embodiment, the method further comprises exposing the feline or sample to a test substance before reacting the polypeptides with the proteins. Then, the comparison is indicative of whether the test substance altered the expression of genes differentially expressed in abnormal felines compared to normal felines, particularly abnormal-associated genes, in the sample.

Animals diagnosed by methods of the present invention as having a kidney disorders, e.g., such as glomemlonephritis, are preferably placed on a kidney protective diet. Kidney protective diets include, for example, diets as described above and in WO2006/119049 A2, WO 2006/071952.

As described in WO2006/119049 A2, in various aspects, the present invention provides methods for (1) prolonging feline life, (2) delaying the onset of feline renal failure, and (3) decreasing the morbidity and mortality caused by feline renal disease. The methods comprise maintaining a feline on a food having reduced levels of protein, phosphorus, and sodium when compared to a standard feline maintenance food. The invention is based upon the novel discovery that feline kidney function can be altered by maintaining a ferine on a food relatively low in protein, phosphorus, and sodium and that altering kidney function can prolong feline life, delay the onset of feline renal failure, and decrease the morbidity and mortality of feline kidney disease.

A "standard feline maintenance food" is a food meeting the nutritional requirements for maintenance of a healthy adult feline, e.g., as set forth by NRC or AAFCO in the herein-cited references, without being "high" in any one of protein, phosphorus, or sodium. A feline food "high" in protein is one having a protein content greater than about 50% of dry matter and/or providing more than about 10 g protein per 100 kcal ME. A feline food "high" in phosphorus is one having a phosphorus content greater than about 1.2% of dry matter and/or providing more than about 0.25 g phosphorus per 100 kcal ME. A feline food "high" in sodium is one having a sodium content greater than about 0.5% of dry matter and/or providing more than about 0.1 g sodium per 100 kcal ME. An illustrative standard feline maintenance food that is not "high" in protein, phosphorus, or sodium comprises, on a dry matter basis, about 45% protein, about 1% phosphorus and about 0.4% sodium, and provides about 9 g protein, about 0.2 g phosphorus and about 0.08 g sodium per 100 kcal ME.

A feline food having "reduced levels" of protein, phosphorus, and sodium is one having sufficiently lower levels than those in a standard feline maintenance food such that a feline consuming the food experiences a prolonged life, a delay the onset of renal failure, and a decrease in the morbidity and mortality associated with kidney disease. Typically, to achieve the benefits of the present invention, levels of protein, phosphorus, and sodium in the food are reduced by at least about 10% from those in a standard feline maintenance food.

In one embodiment wherein each of phosphorus and sodium in the food are reduced by at least about 10% when compared to a standard feline maintenance food, protein is reduced by from about 12% to about 60%, preferably from about 18% to about 48%, from about 24% to about 44%, or from about 30% to about 40%. Protein content of the food, on a dry matter basis, according to this embodiment is from about 18% to about 40%, preferably from about 23% to about 37%, from about 25% to about 34% or from about 27% to about 32%, illustratively from about 28% to about 30%. Expressed on an ME basis, protein content of the food should be from about 3.6 to about 7.9 g/100 kcal ME, preferably from about 4.7 to about 7.4, from about 5.0 to about 6.8 or from about 5.4 to about 6.3 g/100 kcal ME.

In another embodiment wherein each of protein and sodium in the food are reduced by at least about 10% when compared to a standard feline maintenance food, phosphorus is reduced by from about 15% to about 80%, preferably from about 20% to about 75%, from about 30% to about 65%, from about 40% to about 60%, or from about 40% to about 55%. Phosphorus content of the food, on a dry matter basis, according to this embodiment is from about 0.2% to about 0.85%, preferably from about 0.25% to about 0.8%, from about 0.35% to about 0.7%, from about 0.4% to about 0.6%, or from about 0.45% to about 0.6%. Expressed on an ME basis, phosphorus content of the food should be from about 0.04 to about 0.17 g/100 kcal ME, preferably from about 0.05 to about 0.16, from about 0.07 to about 0.14, from about 0.08 to about 0.12, or from about 0.09 to about 0.12 g/100 kcal ME.

In another embodiment wherein each of protein and phosphorus in the food are reduced by at least about 10% when compared to a standard feline maintenance food, sodium is reduced by from about 12% to about 90%, preferably from about 15% to about 80%, from about 18% to about 70% or from about 21% to about 60%. Sodium content of the food, on a dry matter basis, according to this embodiment is from about 0.04% to about 0.35%, preferably from about 0.08% to about 0.34%, from about 0.12% to about 0.33% or from about 0.16% to about 0.32%. In one embodiment sodium content is from about 0.2% to about 0.35%, on a dry matter basis. Expressed on an ME basis, sodium content of the food should be from about 0.008 to about 0.07 g/100 kcal ME, preferably from about 0.016 to about 0.07, from about 0.02 to about 0.07 or from about 0.03 to about 0.06 g/100 kcal ME.

Illustrative canned feline foods wherein each of protein, phosphorus, and sodium are reduced as defined herein include, without limitation, Hill's® Feline k/D®, Hill's Feline k/D® with Chicken, Hill's® Feline g/D®, Hill's Feline l/D®, Purina Veterinary Diet™ NF and Royal Canin Veterinary Diet™ Renal LP 21™. For example, Hill's® Feline k/D® canned food is stated to contain (average nutrient contents): protein: 8.4% as fed, 28.6% dry matter, 6.6 g/100 kcal; phosphorus: 0.10% as fed, 0.34% dry matter, 0.078 g/100 kcal; sodium: 0.09% as fed, 0.31% dry matter, 0.07 g/100 kcal.

Illustrative dry feline foods wherein each of protein, phosphorus, and sodium are reduced as defined herein include, without limitation, Hill's® Feline k/D®, Hill's® Feline g/D®, Hill's® Feline l/D®, Hill's® Science Diet® Adult Ocean Fish & Rice Recipe, Purina Veterinary Diet™ NF and Royal Canin Veterinary Diet™ Renal LP 21™. For example, Hill's® Feline k/D® dry food is stated to contain (average nutrient contents): protein: 26.2% as fed, 28.3% dry matter, 6.7 g/100 kcal; phosphorus: 0.45% as fed, 0.49% dry matter, 0.114 g/100 kcal; sodium: 0.23% as fed, 0.25% dry matter, 0.058 g/100 kcal.

The maintenance of a feline on a food of the present invention is a long-term endeavor. For example, the feline can be maintained on a food according to the present invention for a period of at least about 6 months, at least about 1 year, at least about 2 years, at least about 3 years, or for a period beginning after onset or initial diagnosis of the renal failure or disease and continuing for substantially the remainder of the feline's life. Given the long-term nature of the present methods, it will be understood that it is generally undesirable to restrict any one of protein, phosphorus, and sodium to a level that is below a minimum consistent with overall feline health. According to one embodiment, therefore, protein is not reduced below about 25% dry matter or about 5 g/100 kcal ME. According to another embodiment, phosphorus is not reduced below about 0.45% dry matter or about 0.09 g/100 kcal ME. According to another embodiment, sodium is not reduced below about 0.04% dry matter or about 0.008 g/100 kcal ME.

In one embodiment, the food contains from about 27% to about 32% protein, from about 0.36% to about 0.54% phosphorus, and from about 0.15% to about 0.32% sodium, on a dry matter basis. Such a food typically provides from about 5.4 to about 6.3 g protein, from about 0.08 to about 0.12 g phosphorus, and from about 0.03 to about 0.06 g sodium per 100 kcal ME. Maintenance of felines having a renal disease on such a ration exemplifies the present invention by prolonging life in comparison with a standard feline maintenance food containing about 45% protein, about 0.9% phosphorus, and about 0.4% sodium, that provides about 9 g protein, about 0.2 g phosphorus, and about 0.08 g sodium per 100 kcal ME. The life-prolonging effect of a food as described herein is particularly surprising when it is recognized that the standard food used as a comparator is itself not "high" as defined above in any one of protein, phosphorus or sodium.

In another embodiment, the food comprises a dry food comprising protein in an amount of from about 5% to about 40%, phosphorus in an amount of from about 0.01% to about 2%, and sodium in an amount of from about 0.01% to about 2% on an "as fed" basis. According to this embodiment, on an "as fed" basis, the protein content of the dry food can be from about 10% to about 30%, or from about 24% to about 30%; the phosphorus content can be from about 0.05% to about 1%, or from about 0.2% to about 0.5%; and/or the sodium content can be from about 0.05% to about 1%, or from about 0.15% to about 0.35%.

In another embodiment, the food comprises a moist food comprising protein in an amount of from about 4% to about 12%, phosphorus in an amount of from about 0.03% to about 0.2%, and sodium in an amount of from about 0.03% to about 0.2% on an "as fed" basis. According to this embodiment, on an "as fed" basis, the protein content of the moist food can be from about 5% to about 11%, or from about 6% to about 9%; the phosphorus content can be from about 0.05% to about 0.15%, or from about 0.08% to about 0.1%; and/or the sodium content can be from about 0.05% to about 0.15%, or from about 0.08% to about 0.1%.

Optionally, the food can be modified for nutrients other than protein, phosphorus, and sodium. For example, the food can be supplemented with polyunsaturated fatty acids, more particularly omega-3 fatty acids such as docosahexaenoic acid (DHA) and/or eicosapentaenoic acid (EPA). Many other such modifications are known to skilled artisans.

Dietary allowances may be expressed in relation to metabolizable energy (ME) content of the food, for example in g/MJ or g/100 kcal. Protein herein is expressed as total crude protein unless otherwise indicated. Percentages for compositions herein are expressed on a "dry matter" basis unless specifically stated otherwise.

A further method comprises maintaining a feline on a food having reduced levels of protein, phosphorus, and sodium when compared to a standard feline food while administering one or more renal drugs to the feline for a prescribed period. Typically, health care professionals, e.g., doctors and veterinarians, diagnose kidney disease in a feline and prescribe a renal drug (any drug useful to prevent or treat kidney disease in a feline) to treat the disease. The feline is administered the renal drug until the symptoms cease and the disease is considered cured or administration is continued indefinitely for chronic kidney disease. In the present invention, the feline is maintained on the food having reduced levels of protein, phosphorus, and sodium and renal drugs are administered to the feline for treatment of the disease. Renal drugs useful in the invention are any renal drags known to skilled artisans to be useful for combating kidney disease. Preferred drugs include lysosome-activating compounds such as those described in U.S. Pat. No. 6,589,748, triterpene saponins such as those described in U.S. Pat. No. 6,784,159, activin inhibitors such as those described in U.S. Pat. No. 6,599,876 and US Patent Application Number (USPAN) 20020028762, integrin receptor inhibitors and TGF inhibitors such as those described in U.S. Pat. No. 6,492,325, TGF activation inhibitors such as those described in U.S. Pat. No. 6,458,767, and insulin-like growth factor (IGF) as described in U.S. Pat. No. 5,723,441. Most Preferred drugs include Converting Enzyme (ACE) inhibitors, androgens, erythropoiten, and calcitriol. Angiotensin and endothelin are potent systemic vasoconstrictors with specific intrarenal effects that contribute to progressive renal injury. A variety of renal drugs are used to mitigate the effect of these vasoconstrictors. Angiotensin converting enzyme inhibitors (enalapril—Enacard and Vasotec and benazepril—Lotensin) have been associated with a reduction in the severity of proteinuria and slowing of progression of renal failure. The ACE inhibitor enalapril (Enacard, Vasotec) limits glomerular and systemic hypertension, proteinuria, and glomerular and tubulointerstitial lesions. Angiotensin blockers and endothelin inhibitors have beneficial effects in renal disease. Vasopeptide inhibitors are agents that inhibit both ACE and neutral endopeptidase, an enzyme involved in the breakdown of natriuretic peptides, adrenomedullin, and bradykinin. These renal drugs decrease angiotenin II production and increase accumulation of vasodilators. Renal patients with systemic hypertension respond to calcium channel blockers such as amlodipine (Norvasc). Uremic gastritis (esophagitis, gastritis, gastric ulceration and hemorrhage) is treated with H2 receptor antagonists (cimetidine—Tagamet, famotidine—Pepcid), proton pump blockers (omeprazole—Prilosec), cytoprotective agents (misoprostol—Cytotec), and antiemetic drugs that effect the emetic center (chlorpromazine—Thorazine, perchlorperazine—Compazine, metoclopramide—Reglan). Androgens or anabolic steroids (Stanozol, Winstrol-V) are used in the treatment of anemia associated with chronic renal failure. Hormone replacement therapy using recombinant human (or other species) erythropoiten (Epoetin alpha, Epogen, Procrit) is the treatment of choice for severe anemia associated with renal failure. Phosphate binders (aluminum hydroxide—Amphojel, aluminum carbonate—Basaljel) are used to control hyperphosphatemia and secondary renal hyperparathyroidism. Calcitriol (1,25-dihydroxycholecalciferol) (Rocaltrol) and vitamin D analogues cause a calcium-independent suppression of parathyroid hormone (PTH). Administration of phosphate binders, calcitriol and related compounds has been advocated in chronic renal failure to prevent multi-system toxicity caused by PTH. Potassium depletion and hypokalemia are common in cats with chronic renal failure. Oral supplementation of potassium in the form of potassium gluconate or citrate is recommended. Holistic renal drugs and compositions are also included in the present invention. Preferred holistic renal drugs include cranberry extract and mannose. Cranberry extract is purported to reduce the prevalence of urinary tract infection which is a common risk factor for long-term decline of renal function. Renal drugs include typical small molecule pharmaceuticals, small proteins, macromolecular proteins and molecules, and antibodies and further include vaccines designed to prevent renal disease. Antibodies include polyclonal and monoclonal antibodies and immunoglobulin fragments such as Fv, Fab, Fab', F(ab')2, or other antigen-binding antibody subsequences that interact with an antigen and perform the same biological function as a native antibody. The renal drugs are administered to the feline using any method appropriate for the renal drug and in amounts known to skilled artisans to be sufficient to treat or prevent renal disease.

As described in WO2006/071952, in one aspect, the invention provides compositions for improving kidney function. The compositions comprise both a kidney function improving amount of one or more antioxidants and a reduced amount of protein and/or phosphorus as compared to the maximum amount of protein and phosphorus typically recommended for a healthy animal of the same species or breed. The invention is based upon the discovery that a reduction in certain nutrients in an animal's diet in conjunction with the dietary supplementation of certain antioxidants improves kidney function. Without being bound by theory, it is believed that the improvement results from decreased toxins in the blood due to the reduction of nutrients and decreased presence of oxygen species in the blood due to the presence of antioxidants.

Any antioxidant that can provide improved kidney function can be used in the compositions and methods of the present invention. Suitable antioxidants include, but are not limited to, vitamin E, L-carnitine, a-lipoic acid, and vitamin C. Vitamin E can be in any form suitable for consumption by an animal including, but not limited to, any tocopherol or tocotrienol compound, any enantiomer or racemate thereof, and any mixture of such compounds having vitamin E activity. Vitamin E can be administered as any one or a mixture of different forms or in the form of various derivatives thereof such as esters, including vitamin E acetate, succinate, palmitate and the like, that exhibit vitamin E activity after ingestion by an animal. L-carnitine can be administered as such or in the form of any of various derivatives of carnitine, such as salts, e.g., hydrochloride, fumarate and succinate salts, acetylated carnitine, and the like. a-Lipoic acid can be administered as such, as a lipoate derivative, for example as described in U.S. Pat. No. 5,621,117, or as a racemic mixture, salt, ester or amide thereof. In one embodiment DL-a-lipoic acid is used. Vitamin C can be administered as ascorbic acid, for example L-ascorbic acid, or as various derivatives thereof such as calcium phosphate salt, cholesteryl salt, and ascorbate-2-monophosphate. Salts of vitamin C include, for example, sodium salt, calcium salt, zinc salt and ferrous salt. Esters include, for example, stearate, palmitate and like derivatives. Vitamin C or a derivative thereof can be in any physical form, for example, a liquid, a semisolid, a solid, or a heat stable form that exhibits vitamin C activity after ingestion by the animal. In various embodiments, the compositions comprise various combinations of vitamin E, vitamin C, L-carnitine, and a-lipoic acid.

The compositions of the present invention contain a kidney function improving amount of one or more antioxidants. The amount of antioxidants suitable for improving kidney function for a particular antioxidant is easily determined by the skilled artisan based upon the characteristics of the antioxidant(s). Generally, the composition comprises at least about 10 mg/kg of one or more antioxidants or its equivalent in other units, e.g., IU/kg for vitamin E. For example, compositions of the invention may contain vitamin C and/or vitamin E. In general, the concentration of vitamin C, if present in the compositions of the invention, is at least about 25 mg/kg (or from about 25 to about 2,000 mg/kg, or about 40 to about 1500 mg/kg, or about 50 to about 1000 mg/kg, or about 75 to about 500 mg/kg, or about 100 to about 200 mg/kg) based on the dry weight of the composition. In general, the concentration of vitamin E, if present in the composition of the invention, is at least about 300 IU/kg (or from about 400 to about 1700 IU/kg, or about 500 to about 1400 IU/kg, or about 600 to about 1100 IU/kg, or about 700-800 IU/kg) based on the dry weight of the composition. The weight ratio of vitamin C to vitamin E (as DL-alpha-tocopheryl acetate equivalents) is about 0.2:1 to about 7:1.

To reduce the stress on the kidney of an animal with reduced kidney function, the compositions of the invention also contain a reduced amount of protein and/or phosphorus as compared to the maximum typically recommended for a healthy animal of the same species or breed. For example, it has been recommended that the maximum be 23% of a typical dog's diet comprises protein. See, e.g., Small Animal Clinical Nutrition, 4th ed., p. 223 (2000). In general, the concentration of protein in the compositions of the invention is less than about 23% or less than about 20%, based on the dry weight of the composition. Relatedly, it has been recommended that at least 0.75% of a typical dog's diet comprise phosphorus. See, e.g., Small Animal Clinical Nutrition, 4th ed., p. 223 (2000). In general, the concentration of phosphorus in the dog food compositions of the invention is less than about 0.75%, based on the dry weight of the composition. The concentration of phosphorus in the compositions of the invention may also be less than about 0.60%, based on the dry weight of the composition. The concentrations of phosphorus in the compositions of the invention may also be less than about 0.50%, based on the dry weight of the composition. The weight ratio of protein to phosphorus is about 17:1 to about 110:1. The weight ratio of protein to antioxidants is about 410:1 to about 70:1.

The antioxidants are present at concentrations that are not deleterious to the intended animal's health. Thus, for example, the antioxidants are present at concentrations that do not cause undesirable toxic effects. Also, the protein and phosphorus are present in the compositions of the invention at concentrations that are sufficient to provide the intended animal sufficient dietary protein and phosphorus to maintain the overall health of the animal.

In one aspect, the invention provides a food composition for improving kidney function. The food ingredients useful in the present invention include any food ingredient suitable for consumption by an animal. Typical food ingredients include but are not limited to fats, carbohydrates, proteins, fibers, nutritional balancing agents such as vitamins, minerals, and trace elements, and mixtures thereof. Skilled artisans can select the amount and type of food ingredients for a typical food based upon the dietary requirements of the animal, e.g., the animal's species, age, size, weight, health, and function.

The food ingredient part of the food composition can comprise 100% of any particular food ingredient of can comprise a mixture of food ingredients in various proportions. In preferred embodiments, the food composition comprises a combination of food ingredients in amounts from about 0% to about 50% fat, from about 0% to about 75% carbohydrate, from about 0% to about 95% protein, from about 0% to about 40% dietary fiber, and from about 0% to about 15% of one or more nutritional balancing agents.

The fat and carbohydrate food ingredient is obtained from a variety of sources such as animal fat, fish oil, vegetable oil, meat, meat by-products, grains, other animal or plant sources, and mixtures thereof. Grains include wheat, corn, barley, and rice.

The protein food ingredient is obtained from a variety sources such as plants, animals, or both. Animal protein includes meat, meat by-products, dairy, and eggs. Meats include the flesh from poultry, fish, and animals such as cattle, swine, sheep, goats, and the like, eat by-products include lungs, kidneys, brain, livers, stomachs, and intestines. The protein food ingredient may also be free amino acids and/or peptides. Preferably, the protein food ingredient comprises meat, a meat by-product, dairy products, or eggs.

The fiber food ingredient is obtained from a variety of sources such as vegetable fiber sources, e.g., cellulose, beet pulp, peanut hulls, and soy fiber.

The nutritional balancing agents are obtained from a variety of sources known to skilled artisans, e.g., vitamin and mineral supplements and food ingredients. Vitamins and minerals can be included in amounts required to avoid deficiency and maintain health. These amounts are readily available in the art. The National Research Council (NRC) provides recommended amounts of such nutrients for farm animals. See, e.g., Nutrient Requirements of Swine (10th Rev. Ed., Nat'l Academy Press, Wash. D.C., 1998), Nutrient Requirements of Poultry (9th Rev. Ed., Nat'l Academy Press, Wash. D.C., 1994), Nutrient Requirements of Horses (5th Rev. Ed., Nat'l Academy Press, Wash. D.C., 1989). The American Feed Control Officials (AAFCO) provides recommended amounts of such nutrients for dogs and cats. See American Feed Control Officials, Inc., Official publication, pp. 129-137 (2004). Vitamins generally useful as food additives include vitamin A, vitamin B1, vitamin B2, vitamin B6, vitamin B 12, vitamin D, biotin, vitamin K, folic acid, inositol, niacin, and pantothenic acid. Minerals and trace elements useful as food additives include calcium, phosphorus, sodium, potassium, magnesium, copper, zinc, chloride, iron, selenium, iodine, and iron.

The compositions and food compositions may contain additions ingredients such as vitamins, minerals, fillers, palatability enhancers, binding agents, flavors, stabilizers, emulsifiers, sweeteners, colorants, buffers, salts, coatings, and the like known to skilled artisans. Stabilizers include substances that tend to increase the shelf life of the composition such as preservatives, synergists and sequestrants, packaging gases, stabilizers, emulsifiers, thickeners, gelling agents, and humectants. Examples of emulsifiers and/or thickening agents include gelatin, cellulose ethers, starch, starch esters, starch ethers, and modified starches. Specific amounts for each composition component, food ingredient, and other ingredients will depend on a variety of factors such as the particular components and ingredients included in the composition; the species of animal; the animal's age, body weight, general health, sex, and diet; the animal's consumption rate; the type of kidney disease being treated; and the like. Therefore, the component and ingredient amounts may vary widely and may deviate from the preferred proportions described herein.

In one embodiment, the composition is a food composition that comprises:
  (a) at least about 25 mg/kg (or from about 25 to about 2,000 mg/kg, or about 40 to about 1500 mg/kg, or about 50 to about 1000 mg/kg, or about 75 to about 500 mg/kg, or about 100 to about 200 mg/kg) vitamin C, based on the dry weight of the composition;
  (b) at least about 300 IU/kg (or from about 300 to about 2000 IU/kg, or about 500 to about 1400 IU/kg, or about 600 to about 1100 IU/kg, or about 700-800 IU/kg) vitamin E, based on the dry weight of the composition;
  (c) less than about 25% (or less than about 20%) protein, based on the dry weight of the composition; and
  (d) less than about 1.0% (or less than about 0.75%, or less than about 0.60%) phosphorus, based on the dry weight of the composition.

In such an embodiment, the composition also may, for example, comprise at least one of the following:
  (a) from about 0% to about 75% carbohydrate,
  (b) from about 2% to about 50% fat,
  (c) from about 0% to about 40% dietary fiber, and
  (d) from about 0% to about 15% of one or more nutritional balancing agents.

In another embodiment, the composition comprises from about 25 to about 2000 mg/kg vitamin C, from about 300 to about 2000 IU/kg vitamin E, from about 14% to about 23% protein, and from about 0.2% to about 0.75% phosphorus.

Food compositions may be prepared in a canned or wet form using conventional food preparation processes known to skilled artisans. Typically, ground animal proteinaceous tissues are mixed with the other ingredients such as fish oils, cereal grains, balancing ingredients, special purpose additives (e.g., vitamin and mineral mixtures, inorganic salts, cellulose and beet pulp, bulking agents, and the like) and water in amounts sufficient for processing. These ingredients are mixed in a vessel suitable for heating while blending the components. Heating of the mixture is effected using any suitable manner, e.g., direct steam injection or using a vessel fitted with a heat exchanger. Following the addition of the last ingredient, the mixture is heated to a temperature of from about 50° F. to about 212° F. Temperatures outside this range are acceptable but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. Sterilization is usually accomplished by heating to temperatures of greater than about 230° F. for an appropriate time depending on the temperature used, the composition, and similar factors. The compositions of the present invention can be added to the food compositions before, during, or after preparation.

Food compositions may be prepared in a dry form using conventional processes known to skilled artisans. Typically, dry ingredients such as animal protein, plant protein, grains, and the like are ground and mixed together. Moist or liquid ingredients, including fats, oils, animal protein, water, and the like are then added to and mixed with the dry mix. The mixture is then processed into kibbles or similar dry pieces. Kibble is often formed using an extrusion process in which the mixture of dry and wet ingredients is subjected to mechanical work at a high pressure and temperature and forced through small openings and cut off into kibble by a rotating knife. The wet kibble is then dried and optionally coated with one or more topical coatings such as flavors, fats, oils, powders, and the like. Kibble also can be made from the dough using a baking process, rather than extrusion, wherein the dough is placed into a mold before dry-heat processing. The food compositions can be in the form of a treat using an extrusion or baking process similar to those described above for dry food or a toy such as those disclosed in U.S. Pat. Nos. 5,339,771 and 5,419,283. The compositions of the present invention can be added to the food compositions before, during, or after preparation.

Treats include compositions that are given to an animal to entice the animal to eat during a non-meal time, e.g., dog bones for canines. Treats may be nutritional wherein the composition comprises one or more nutrients or and may have a food-like composition. Non-nutritional treats encompass any other treats that are non-toxic. The composition or components are coated onto the treat, incorporated into the treat, or both. Treats of the present invention can be prepared by an extrusion or baking process similar to those used for dry food. Other processes also may be used to either coat the composition on the exterior of existing treat forms or inject the composition into an existing treat form.

Supplements include a feed used with another feed to improve the nutritive balance or performance of the total. Supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials, Inc. Official Publication, p. 220 (2003). Supplements may be in various forms including, for example, powders, liquids, syrups, pills, encapsulated compositions, etc.

The antioxidants of the invention may be incorporated into the composition during the processing of the formulation, such as during and/or after mixing of other components of the composition. Distribution of these components into the composition can be accomplished by conventional means.

In another aspect, the present invention provides the compositions and food compositions of the present invention further comprising one or more renal drugs. Renal drugs useful in the invention are any renal drugs known to skilled artisans to be useful for improving kidney function or combating kidney disease. Preferred drugs include lysosome-activating compounds such as those described in U.S. Pat. No. 6,589,748, triterpene saponins such as those described in U.S. Pat. No. 6,784,159, activin inhibitors such as those described in U.S. Pat. No. 6,599,876 and US Patent Application Number (USPAN) 20020028762, integrin receptor inhibitors and TGF inhibitors such as those described in U.S. Pat. No. 6,492,325, TGF activation inhibitors such as those described in U.S. Pat. No. 6,458,767, and insulin-like growth factor (IGF) as described in U.S. Pat. No. 5,723,441. Most Preferred drugs include Converting Enzyme (ACE) inhibitors, androgens, erythropoiten, and calcitriol. Angiotensin and endothelin are potent systemic vasoconstrictors with specific intrarenal effects that contribute to progressive renal injury. A variety of renal drugs are used to mitigate the effect of these vasoconstrictors. Angiotensin converting enzyme inhibitors (enalapril—Enacard and Vasotec and benazepril—Lotensin) have been associated with a reduction in the severity of proteinuria and slowing of progression of renal failure. The ACE inhibitor enalapril (Enacard, Vasotec) limits glomerular and systemic hypertension, proteinuria, and glomerular and tubulointerstitial lesions. Angiotensin blockers and endothelin inhibitors have beneficial effects in renal disease. Vasopeptide inhibitors are agents that inhibit both ACE and neutral endopeptidase, an enzyme involved in the breakdown of natriuretic peptides, adrenomedullin, and bradykinin. These renal drugs decrease angiotenin II production and increase accumulation of vasodilators. Renal animals with systemic hypertension respond to calcium channel blockers such as amlodipine (Norvasc). Uremic gastritis (esophagitis, gastritis, gastric ulceration and hemorrhage) is treated with H2 receptor antagonists (cimetidine—Tagamet, famotidine—Pepcid), proton pump blockers (omeprazole—Prilosec), cytoprotective agents (misoprostol—Cytotec), and antiemetic drugs that effect the emetic center (chlorpromazine—Thorazine, perchlorperazine—Compazine, metoclopramide—Reglan). Androgens or anabolic steroids (Stanozol, Winstrol-V) are used in the treatment of anemia associated with chronic renal failure. Hormone replacement therapy using recombinant human (or other species) erythropoiten (Epoetin alpha, Epogeh, Procrit) is the treatment of choice for severe anemia associated with renal failure. Phosphate binders (aluminum hydroxide—Amphojel, aluminum carbonate—Basaljel) are used to control hyperphosphatemia and secondary renal hyperparathyroidism. Calcitriol (1, IS-dihydroxycholecalciferol) (Rocaltrol) and vitamin D analogues cause a calcium-independent suppression of parathyroid hormone (PTH). Administration of phosphate binders, calcitriol and related compounds has been advocated in chronic renal failure to prevent multi-system toxicity caused by PTH. Potassium depletion and hypokalemia are common in cats with chronic renal failure. Oral supplementation of potassium in the form of potassium gluconate (Tumil K, RenaKare, Kolyum) or citrate is recommended. Holistic renal drugs and compositions are also included in the present invention. Preferred holistic renal drugs include cranberry extract and mannose. Cranberry extract is purported to reduce the prevalence of urinary tract infection which is a common risk factor for long-term decline of renal function. Renal drugs include typical small molecule pharmaceuticals, small proteins, macromolecular proteins and molecules, and antibodies and further include vaccines designed to improve kidney function and/or prevent renal disease. Antibodies include polyclonal and monoclonal antibodies and immunoglobulin fragments such as Fv, Fab, Fab', F(ab')2, or other antigen-binding antibody subsequences that interact with an antigen and perform the same biological function as a native antibody. The renal drugs are administered to the animal using any method appropriate for the renal drug and in amounts known to skilled artisans to be sufficient to improve kidney function and/or treat or prevent renal disease.

The invention thus provides, a method (Method 1) of diagnosing the existence of a kidney disorder in a feline comprising measuring the level of expression of one or more biomarkers selected from the group consisting of lumican (LUM); collagen alpha 1(III) chain, variant 12 (COL3A1); decorin (DCN); secreted frizzled-related protein 2 (SFRP2); retinol binding protein 5 (rbp5); MMP-2; MMP-7; and MMP-19, in a biological sample from the feline, wherein differences in expression of the one or more biomarkers in the sample relative to a control value for expression in a sample from a normal animal indicates the existence of a kidney disorder, e.g. according to any of the following methods:

1.1. Method 1 wherein the level of expression of the one or more biomarkers is determined by measuring gene expression of the one or more biomarkers using either (i) a DNA microarray comprising one or more oligonucleotides complementary to mRNA or cDNA corresponding to the one or more biomarkers to be measured, or (ii) a quantitative polymerase chain reaction with oligonucleotide primers for mRNA or cDNA corresponding to the one or more biomarkers to be measured, e.g.,
   a. The foregoing method wherein the step of measuring gene expression of one or more biomarkers comprises (i) isolating RNA from the tissue sample, (ii) reverse transcribing the RNA to obtain the corresponding cDNA, (iii) isolating and fragmenting the cDNA thus obtained, (iv) contacting the cDNA fragments with a DNA microarray comprising one or more oligonucleotides complementary to cDNA corresponding to the one or more biomarkers to be measured, and (v) detecting hybridization between the cDNA fragments and the one or more oligonucleotides in the DNA microarray.
   b. The foregoing method wherein the oligonucleotides in the DNA microarray comprise one or more probes capable of hybridizing to one or more of SEQ ID NOS. 9-16.
   c. The foregoing method wherein the oligonucleotides in the DNA microarray comprise one or more probes comprising sequences selected from one or more of SEQ ID NOS. 1-8.
   d. Any of the preceding methods involving detecting hybridization wherein the hybridization between the cDNA fragments and the one or more oligonucleotides in the DNA microarray is under stringent conditions.
1.2. Method 1 wherein the level of expression of the biomarker is detected by an antibody to the expressed protein.
   a. Method 1.2 wherein the biomarker is detected by an immunoassay selected from a competitive binding assay, a non-competitive binding assay, a radioimmunoassay, an enzyme linked immunosorbent assay (ELISA), a sandwich assay, a precipitin reaction, a gel diffusion immunodiffusion assay, an agglutination assay, a fluorescent immunoassay, chemiluminescence immunoassay, immunoPCR immunoassay, a protein A or protein G immunoassay and an immunoelectrophoresis assay.
   b. The foregoing method which is an enzyme-linked immunosorbent assay (ELISA).
   c. Method 1.2 wherein the assay is a lateral flow immunochromatographic assay.
   d. Method 1.2 wherein the biological sample is blood or urine.
1.3. Method 1 wherein the level of expression of the biomarker is detected by quantitative mass spectroscopy measuring the expressed protein in the biological sample, e.g., wherein the biological sample is blood or urine.
1.4. Method 1 wherein the level of expression of the biomarker is detected by an aptamer recognizing the expressed protein.
   a. Method 1.4 wherein the aptamer is an oligonucleotide.
   b. Method 1.4 wherein the aptamer is a peptide.
   c. Method 1.4 wherein the biological sample is blood or urine.
1.5. Any of the preceding methods wherein the level of expression of the one or more biomarkers in the biological sample relative to a control value for expression in normal sample is greater than two-fold, e.g., greater than five-fold, or less than one half.
1.6. Any of the preceding methods wherein the level of expression of the one or more biomarkers in the biological sample is at least one standard deviation higher or lower than the mean expression of the biomarkers in a normal sample.
1.7. Any of the preceding methods wherein the level of expression of the one or more biomarkers in the biological sample is normalized relative to expression of one or more genes known to have relatively constant expression.
1.8. Any of the preceding methods wherein the biological sample is a sample of renal tissue.
1.9. Any of the preceding methods wherein the biological sample is blood.
1.10. Any of the preceding methods comprising detecting expression levels of secreted frizzle-related protein-2 (SFRP2) and/or retinol binding protein 5 (rbp5).
1.11. Any of the preceding methods comprising detecting expression levels of secreted frizzle-related protein-2 (SFRP2) and/or retinol binding protein 5 (rbp5) and, optionally, expression levels of at least one gene selected from the group consisting of: lumican (LUM); decorin (DCN), collagen alpha 1 (III) chain, variant 12 (COL3A1)); matrix metalloproteinase-2 (MMP2); matrix metalloproteinase-7 (MMP7); and matrix metalloproteinase-19 (MMP19).
1.12. Any of the preceding methods wherein the kidney disorder is at an early stage, e.g., wherein the feline has essentially normal kidney function, e.g., as measured by one or more of the following: normal glomerular filtration rate, creatinine clearance rate, urinary protein levels, serum creatinine levels, urinary creatinine levels, blood urea nitrogen (BUN) levels, radioisotope metabolic labeling, soft tissue imaging, including sonography, magnetic resonance imaging and/or computed tomography.
1.13. Any of the foregoing methods wherein the kidney disorder is a disorder characterized by an abnormal loss of renal function, renal failure, reduced glomerular filtration rate or glomerulonephritis.
1.14. Any of the foregoing methods wherein the kidney disorder is glomerulonephritis.
1.15. Any of the preceding methods wherein kidney disorder is indicated by a significant difference in expression of one or more of the following relative to control expression values (for example, wherein a "significant difference" in the case of increase expression is an increase of at least twofold and in the case of decreased expression is a decrease of at least 50%):
   Lumican expression increased;
   Collagen alpha 1(III) chain, variant 12 expression increased;
   Decorin expression increased;
   Secreted frizzled-related protein 2 expression increased;
   Retinol Binding Protein 5 expression decreased;
   MMP-2 expression increased;
   MMP-7 expression increased; and/or
   MMP-19 expression increased.

In a further embodiment, the invention provides a method (Method 2) of treating, ameliorating, or delaying the progression of a kidney disorder in a feline in need thereof, comprising diagnosing the existence of a kidney disorder e.g., using Method 1, et seq., and managing the condition, for example by a diet and/or medication. For example, the invention provides:
   2.1. Method 2 comprising providing a kidney protective diet as substantially the sole diet to a feline having a kidney disorder as diagnosed or diagnosable by the method of any of Methods 1, et seq.

2.2. Method 2 or 2.1 wherein the feline has essentially normal kidney function, e.g., as measured by one or more of the following: normal glomerular filtration rate, creatinine clearance rate, urinary protein levels, serum creatinine levels, urinary creatinine levels, blood urea nitrogen (BUN) levels, radioisotope metabolic labeling, soft tissue imaging, including sonography, magnetic resonance imaging and/or computed tomography.

2.3. Any of the foregoing methods wherein the feline is at least five years of age.

2.4. Any of the foregoing methods wherein the disorder is a disorder characterized by an abnormal loss of renal function, renal failure, reduced glomerular filtration rate or glomerulonephritis.

2.5. Any of the foregoing methods wherein the kidney disorder is glomerulonephritis.

2.6. Any of the foregoing methods wherein the feline has been identified as having renal disease.

2.7. Any of the foregoing methods wherein the feline is maintained on the kidney protective diet for a period of at least about 6 months.

2.8. Any of the foregoing methods wherein the feline is maintained on the kidney protective diet for a period beginning after onset or initial diagnosis of renal disease and continuing for substantially the remainder of the life of the feline.

2.9. Any of the foregoing methods wherein the kidney protective diet comprises one or more of the following modifications relative to a standard feline diet:
Reduced phosphorus
Reduced levels of protein
Reduced sodium
Increased levels of omega-3 fatty acids
Increased levels of B-complex vitamins
Increased antioxidants.

2.10. Any of the foregoing methods wherein the kidney protective diet comprises from about 18% to about 40% protein, from about 0.2% to about 0.85% phosphorus, and from about 0.04% to about 0.35% sodium, on a dry matter basis.

2.11. Any of the foregoing methods wherein the kidney protective diet provides from about 3.6 to about 7.9 g/100 kcal ME protein, from about 0.04 to about 0.17 g/100 kcal ME phosphorus, and from about 0.008 to about 0.07 g/100 kcal ME sodium.

2.12. Any of the foregoing methods wherein the kidney protective diet comprises a dry food comprising protein in an amount of from about 5% to about 40%, phosphorus in an amount of from about 0.01% to about 2%, and sodium in an amount of from about 0.01% to about 2%, on an "as fed" basis.

2.13. Any of the foregoing methods wherein the kidney protective diet comprises a moist food comprising protein in an amount of from about 4% to about 12%, phosphorus in an amount of from about 0.03% to about 0.2%, and from sodium in an amount of from about 0.03% to about 0.2%, on an "as fed" basis.

In a further embodiment, the invention provides reagents, optionally labeled, useful in the detection of the level of expression of one or more biomarkers selected from the group consisting of lumican; collagen alpha 1(III) chain, variant 12; decorin; secreted frizzled-related protein 2; retinol binding protein 5; MMP-2; MMP-7; and MMP-19 in a feline, e.g., a. Antibodies, for example monoclonal antibodies, single chain antibodies, and functional antibody fragments, recognizing feline proteins selected from the group consisting of lumican; collagen alpha 1(III) chain, variant 12; decorin; secreted frizzled-related protein 2; retinol binding protein 5; MMP-2; MMP-7; and MMP-19.

b. Aptamers, for example nucleic acid or peptidic aptamers, recognizing feline proteins selected from the group consisting of lumican; collagen alpha 1(III) chain, variant 12; decorin; secreted frizzled-related protein 2; retinol binding protein 5; MMP-2; MMP-7; and MMP-19.

c. Isolated and purified or recombinant feline protein selected from the group consisting of lumican; collagen alpha 1(III) chain, variant 12; decorin; secreted frizzled-related protein 2; retinol binding protein 5; MMP-2; MMP-7; and MMP-19.

d. Oligonucleotide probes capable of hybridizing to a feline gene selected from the group consisting of lumican; collagen alpha 1(III) chain, variant 12; decorin; secreted frizzled-related protein 2; retinol binding protein 5; MMP-2; MMP-7; and MMP-19, e.g., capable of hybridizing to one or more of SEQ ID NOS. 9-16, e.g. selected from one or more of SEQ ID NOS. 1-8.

In a further embodiment, the invention provides a kit (Kit 1) for the diagnosis, prognosis or monitoring a kidney disorder in a feline, comprising a. means for measuring gene expression of one or more biomarkers selected from the group consisting of lumican; collagen alpha 1(III) chain, variant 12; decorin; secreted frizzled-related protein 2; retinol binding protein 5; MMP-2; MMP-7; and MMP-19 in a biological sample from the feline, and b. instructions for using such means to measure expression of the one or more biomarkers in a biological sample from the feline and evaluating the presence of a process leading to a kidney disorder in the feline, e.g.

1.1 Kit 1 wherein the means for measuring the one or more biomarkers is one or more nucleic acid probes capable of detecting gene expression of the one or more biomarkers;

1.2 Kit 1.1 wherein the one or more nucleic acid probes are capable of hybridizing to one or more of SEQ ID NOS. 9-16, e.g., under stringent conditions;

1.3 Kit 1.2 wherein the one or more nucleic acid probes comprise a sequence or sequences selected from one or more of SEQ ID NOS. 1-8.

1.4 Any of the preceding kits comprising a DNA microarray comprising one or more nucleic acid probes capable of detecting gene expression of the one or more biomarkers.

1.5 Kit 1 wherein the means for measuring the one or more biomarkers is one or more antibodies capable of detecting gene expression of the one or more biomarkers by recognizing the expressed protein.

1.6 Kit 1.5 in ELISA format comprising antibody capable of detecting the one or more biomarkers; isolated, purified or recombinant protein corresponding to the expressed protein; and buffer.

1.7 Kit 1 wherein the means for measuring the one or more biomarkers is one or more aptamers, e.g., as hereinbefore described, capable of detecting gene expression of the one or more biomarkers by recognizing the expressed protein.

1.8 Any of the foregoing Kits wherein the one or more biomarkers include secreted frizzle-related protein-2 (SFRP2) and/or retinol binding protein 5 (rbp5);

1.9 Any of the foregoing kits adapted for use in any of the foregoing Method 1 et seq. or Method 2, et seq.

The invention further provides the use
of a nucleotide sequence corresponding to or complementary to a gene for feline lumican; collagen alpha 1(III)

chain, variant 12; decorin; secreted frizzled-related protein 2; retinol binding protein 5; MMP-2; MMP-7; and MMP-19, e.g., a nucleotide sequence corresponding to or complementary to any of SEQ ID NO 1-16, or of an antibody to a protein selected from feline lumican; collagen alpha 1(III) chain, variant 12; decorin; secreted frizzled-related protein 2; retinol binding protein 5; MMP-2; MMP-7; and MMP-19, or of an aptamer to a protein selected from feline lumican; collagen alpha 1(III) chain, variant 12; decorin; secreted frizzled-related protein 2; retinol binding protein 5; MMP-2; MMP-7; and MMP-19, or isolated, purified or recombinant feline lumican; collagen alpha 1(III) chain, variant 12; decorin; secreted frizzled-related protein 2; retinol binding protein 5; MMP-2; MMP-7; and MMP-19, in a method according to Method 1, et seq. or Method 2 et seq, or in the manufacture of a kit according to Kit 1, et seq.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1A:
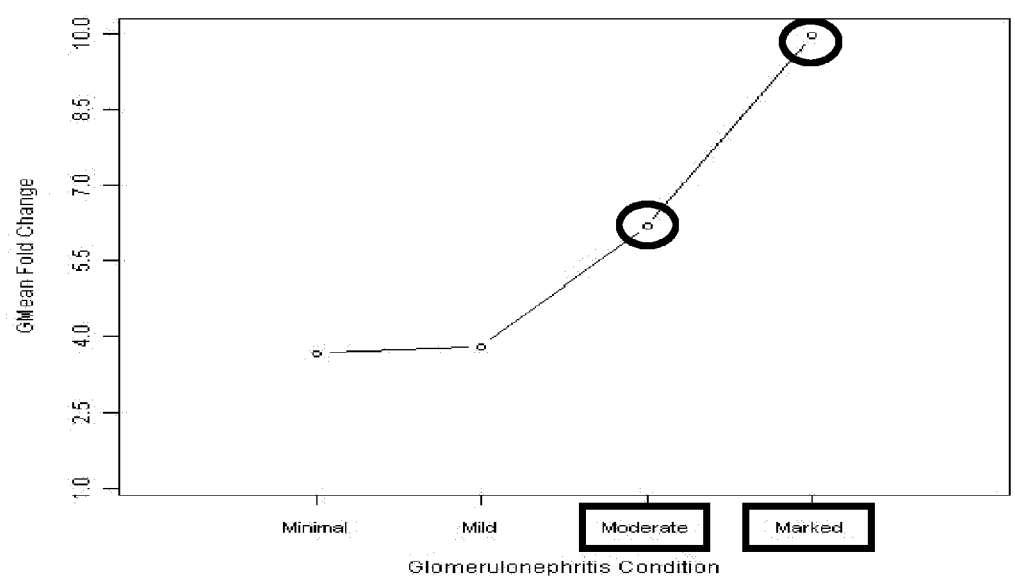
FIG. 1a is a plot of the geographic mean fold change versus the stage of glomerulonephritis of a subject feline for the expression of the gene *Canis familiaris* similar to lumican precursor (keratan sulfate proteoglycan lumican) mRNA.

The following description of the preferred embodiments is merely exemplary in nature and is in no way intended to limit the invention, its application, or uses.

Certain Definitions

As used herein and in the appended claims, the singular forms "a," "an," and "the" include plural references unless the context clearly dictates otherwise, e.g., reference to "a variant" includes a plurality of variants. Further, defined terms include variations of the terms used in the proper grammatical context, e.g., the term "specifically binds" includes "specific binding" and other forms of the term. Similarly, the words "comprise," "comprises," and "comprising" are to be interpreted inclusively rather than exclusively.

The term "antibody" means any immunoglobulin that binds to a specific antigen, including IgG, IgM, IgA, IgD, and IgE antibodies. The term includes polyclonal, monoclonal, monovalent, humanized, heteroconjugate, antibody compositions with polyepitopic specificity, chimeric, bispecific antibodies, diabodies, single-chain antibodies, and antibody fragments such as Fab, Fab', F(ab')$_2$, and Fv, or other antigen-binding fragments.

The term "array" means an ordered arrangement of at least two probes on a substrate. At least one of the probes is a control or standard and at least one of the probes is a diagnostic probe. The arrangement of from about two to about 40,000 probes on a substrate assures that the size and signal intensity of each labeled complex formed between a probe and a sample polynucleotide or polypeptide is individually distinguishable. The collection of molecules deposited on the array may be prepared either synthetically or biosynthetically. The array may take a variety of forms including libraries of soluble molecules, libraries of compounds tethered to resin beads, silica chips or other solid supports. The nucleic acid array may include libraries of nucleic acids which can be prepared by spotting nucleic acids in essentially any length (for example, from 1 to about 1,000 nucleotides in length) onto a substrate. A nucleic acid probe array preferably comprises nucleic acids bound to a substrate in known locations. In other embodiments, the system may include a solid support or substrate, such as a membrane, filter, microscope slide, microwell, sample tube, bead, bead array, or the like. The solid support may be made of various materials, including paper, cellulose, nylon, polystyrene, polycarbonate, plastics, glass, ceramic, stainless steel, or the like. The solid support may preferably have a rigid or semi-rigid surface, and may preferably be spherical (e.g., bead) or substantially planar (e.g., flat surface) with appropriate wells, raised regions, etched trenches, or the like. The solid support may also include a gel or matrix in which nucleic acids may be embedded.

The term "biomarkers" refers to genes and gene products encoded by a gene of the invention or a homolog thereof, especially a feline homolog thereof, wherein the gene has been determined to have been differentially expressed as a result of a disease, condition, disorder or the administration of a substance, drug, nutrient or dietary component or combinations thereof, and wherein such genes and gene products of the invention are identified in SEQ ID) NOS.: 9, 10, 11, 12, 13, 14, 15, and 16 or a homologous gene thereof including, without limitation a feline gene. A biomarker may be a polynucleotide, polypeptide, protein, RNA, including an RNA transcript or its translation product, DNA, cDNA, a metabolite of one or more of the foregoing molecules, or a useful variant of any one of the foregoing molecules, the differential expression of which is associated with a kidney disorder, including, without limitation glomerulonephritis, and wherein the correlation of such differential expression in a sample taken from a test animal to a sample taken from a control animal can be used in the diagnosis, prognosis, monitoring or treatment of condition, disease or disorder in an animal in need thereof. In addition, a biomarker can be generally used to refer to any portion or segment of such gene or protein that can identify or correlate with the full-length gene or protein, for example, in an assay or other method of the invention. Biomarker expression can also be identified by detection of biomarker translation (i.e., detection of biomarker protein in a sample). Methods suitable for the detection of biomarker protein include any suitable method for detecting and/or measuring proteins from a cell or cell extract. Such methods include, but are not limited to, immunoblot (e.g., Western blot), enzyme-linked immunosorbent assay (ELISA), radioimmunoassay (RIA), immunoprecipitation, immunohistochemistry and immunofluorescence. Particularly preferred methods for detection of proteins include any single-cell assay, including immunohistochemistry and immunofluorescence assays. Such methods are well known in the art. Furthermore, antibodies against certain of the biomarkers described herein are known in the art and are described in the public literature, and methods for their preparation are well known to the skilled worker.

The term "comparably" as used to compare expression of a test sample to a control sample shall mean indicia of like character and quantity and shall include, without limitation, values within one standard deviation around the mean value to which said comparison is made and values encompassing differential expression between the test sample and control sample.

The terms "differentially expressed gene," "differential gene expression." "differential expression" or "differentially expressed" and their synonyms, which are used interchangeably, refer to a gene whose expression is activated to a higher or lower level in a subject suffering from a disease, condition, or disorder, or as a result of the being administered a substance, drug, nutrient or dietary component or combinations thereof, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, condition, or disorder, or as a result of being administered a substance, drug, nutrient or dietary component or combinations thereof, or between various stages of the same disease, condition, or disorder, or as a result of being administered different amounts of a substance, drug, nutrient or dietary component or combinations thereof. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about 2.0, 1.9, 1.8, 1.7, 1.6, 1.5, 1.4, 1.3, 1.2, 1.1 or 1.0-fold, preferably at least about two-fold or more, more preferably at least about 2.5, 3 or 4 or more fold change in the amount of transcribed polynucleotides or translated protein in a sample.

The term "fold" when used as a measure of differential gene expression means an amount of gene expression in a feline that is a multiple or a fraction of gene expression compared to the amount of gene expression in a comparison feline, e.g., a feline having a loss of renal function, renal failure, a reduced glomerular filtration rate or glomerulonephritis compared to an animal not demonstrating such a condition. For example, a gene that is expressed 2 times as much in the animal as in the comparison animal has a 2-fold differential gene expression and a gene that is expressed one-half as much in the animal as in the comparison animal also has a 2-fold differential gene expression.

The term "fragment" means (1) an oligonucleotide or polynucleotide sequence that is a portion of a complete sequence and that has the same or similar activity for a particular use as the complete polynucleotide sequence or (2) a peptide or polypeptide sequence that is a portion of a complete sequence and that has the same or similar activity for a particular use as the complete polypeptide sequence. Such fragments can comprise any number of nucleotides or amino acids deemed suitable for a particular use. Generally, oligonucleotide or polynucleotide fragments contain at least about 10, 50, 100, or 1000 nucleotides and polypeptide fragments contain at least about 4, 10, 20, or 50 consecutive amino acids from the complete sequence. The term encompasses polynucleotides and polypeptides variants of the fragments. A polynucleotide, for example, can be broken up, or fragmented into, a plurality of segments.

Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," 3rd Ed. Cold Spring Harbor Laboratory Press, Cold Spring Harbor, N.Y. (2001) ("Sambrook et al."), which is incorporated herein by reference for all purposes. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

The term "gene" or "genes" means a complete or partial segment of DNA involved in producing a polypeptide, including regions preceding and following the coding region (leader and trailer) and intervening sequences (introns) between individual coding segments (exons). The term encompasses any DNA sequence that hybridizes to the complement of gene coding sequences.

The term "homolog" means (1) a polynucleotide, including polynucleotides from the same or different animal species, having greater than 30%, 50%, 70%, 90%, 91%, 92%, 93%, 94%, 95%, 96%, 97%, 98% or 99% sequence similarity to a polynucleotide and having the same or substantially the same properties and performing the same or substantially the same function as the complete polynucleotide, or having the capability of specifically hybridizing to a polynucleotide under stringent conditions or (2) a polypeptide, including polypeptides from the same or different animal species, having greater than 30%, 50%, 70%, 90%, 91%, 92%, 93%, 94%, 95%, 96%, 97%, 98% or 99% sequence similarity to a polypeptide identified by the expression of polynucleotides and having the same or substantially the same properties and performing the same or substantially the same function as the complete polypeptide, or having the capability of specifically binding to a polypeptide identified by the expression of polynucleotides. Sequence similarity of two polypeptide sequences or of two polynucleotide sequences is determined using methods known to skilled artisans, e.g., the algorithm of Karlin and Altschul (Proc. Natl. Acad. Sci. USA 87:2264-2268 (1990)). Such an algorithm is incorporated into the NBLAST and XBLAST programs of Altschul et al. (J. Mol. Biol. 215:403-410 (1990)). To obtain gapped alignments for comparison purposes, Gapped Blast can be utilized as described in Altschul et al. (Nucl. Acids Res. 25: 3389-3402 (1997)). When utilizing BLAST and Gapped BLAST programs, the default parameters of the respective programs (e.g., XBLAST and NBLAST) are used. See http://www.ncbi.nlm.nih.gov.

The term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid." The proportion of the population of polynucleotides that forms stable hybrids is referred to herein as the "degree of hybridization."

Hybridization reactions can be performed in absolute or differential hybridization formats. In the absolute hybridization format, polynucleotides derived from one sample are hybridized to the probes in a nucleic acid array. Signals detected after the formation of hybridization complexes correlate to the polynucleotide levels in the sample. In the differential hybridization format, polynucleotides derived from two samples are labeled with different labeling moieties. A mixture of these differently labeled polynucleotides is added to a nucleic acid array. The nucleic acid array is then examined under conditions in which the emissions from the two different labels are individually detectable. In one embodiment, the fluorophores Cy3 and Cy5 (Amersham Pharmacia Biotech, Piscataway, N.J.) are used as the labeling moieties for the differential hybridization format.

Signals gathered from nucleic acid arrays can be analyzed using commercially available software, such as those provided by Affymetrix or Agilent Technologies. Controls, such as for scan sensitivity, probe labeling and cDNA or cRNA quantization, are preferably included in the hybridization experiments. Hybridization signals can be scaled or normalized before being subject to further analysis. For instance, hybridization signals for each individual probe can be normalized to take into account variations in hybridization intensities when more than one array is used under similar test conditions. Hybridization signals can also be normalized using the intensities derived from internal normalization controls contained on each array. In addition, genes with relatively consistent expression levels across the samples can be used to normalize the expression levels of other genes. In one embodiment, probes for certain maintenance genes are included in a nucleic acid array of the present invention. These genes are chosen because they show stable levels of expression across a diverse set of tissues. Hybridization signals can be normalized and/or scaled based on the expression levels of these maintenance genes.

The term "hybridization complex" means a complex that is formed between sample polynucleotides when the purines of one polynucleotide hydrogen bond with the pyrimidines of the complementary polynucleotide, e.g., 5'-A-G-T-C-3' base pairs with 3'-T-C-A-G-5'. The degree of complementarily and the use of nucleotide analogs affect the efficiency and stringency of hybridization reactions.

The term "hybridization probes" includes nucleic acids (such as oligonucleotides) capable of binding in a base-specific manner to a complementary strand of nucleic acid. Such probes include peptide nucleic acids, as described in Nielsen et al., Science 254:1497-1500 (1991), Nielsen Curr. Opin. Biotechnol., 10:71-75 (1999) and other nucleic acid analogs and nucleic acid mimetics. See U.S. Pat. No. 6,156,501 filed Apr. 3, 1996.

The term "kidney disease" or "kidney disorder" or analogously "renal disease" or "renal disorder" is intended to cover an acute or chronic abnormal loss of kidney function, such as renal failure, reduced glomerular filtration rate and glomerulonephritis. Glomerulonephritis may take the form of membranous glomerulonephritis which involves thickening of the glomerular basement membrane. Alternatively, glomerulonephritis may take the form of proliferative or mesangioproliferative glomerulonephritis, which is characterized by proliferation of cells in the mesangial matrix. In addition, glomerulonephritis may take the form of membranoproliferative glomerulonephritis which involves a combination of the foregoing changes. Glomerulosclerosis is a severe form of glomerulonephritis. Kidney disease or kidney disorders also include nephritis, nephropathy, hyperfiltration, mild microalbuminuria, clinical albuminuria, advanced clinical nephropathy, chronic renal insufficiency, injuries to renal papilla, tubular necrosis and diabetic nephropathy, all as differentially diagnosed by veterinarians of ordinary skill in the art. The term is not intended to encompass polycystic kidney disease of genetic origin.

A feline with normal renal function is a feline that is asymptomatic for a kidney disorder and demonstrates no clinical signs or symptoms of a kidney disorder and no changes in clinical laboratory measurements of renal function. Normal renal function may be determined by one or more measurements of, including, without limitation, glomerular filtration rate, urine protein level, blood creatinine level, urine creatinine level, creatinine clearance and blood urea nitrogen.

"Nucleic acid sequence" means an oligonucleotide, nucleotide or polynucleotide, and fragments or portions thereof, and to DNA or RNA of genomic or synthetic origin which may be single- or double-stranded, and represent the sense or antisense strand.

The term "polynucleotide" or "oligonucleotide" means a polymer of nucleotides. The term encompasses DNA and RNA (including cDNA and mRNA) molecules, either single or double stranded and, if single stranded, its complementary sequence in either linear or circular form. The term also encompasses fragments, variants, homologs, and alleles, as appropriate for the sequences that have the same or substantially the same properties and perform the same or substantially the same function as the original sequence. The sequences may be fully complementary (no mismatches) when aligned or may have up to about a 30% sequence mismatch. Preferably, for polynucleotides, the chain contains from about 20 to 10,000 nucleotides, more preferably from about 150 to 3,500 nucleotides. Preferably, for oligonucleotides, the chain contains from about 2 to 100 nucleotides, more preferably from about 6 to 30 nucleotides. The exact size of a polynucleotide or oligonucleotide will depend on various factors and on the particular application and use of the polynucleotide or oligonucleotide. The term includes nucleotide polymers that are synthesized and that are isolated and purified from natural sources. The term "polynucleotide" is inclusive of "oligonucleotide."

The term "polypeptide," "peptide," or "protein" means a polymer of amino acids. The term encompasses naturally occurring and non-naturally occurring (synthetic) polymers and polymers in which artificial chemical mimetics are substituted for one or more amino acids. The term also encompasses fragments, variants, and homologs that have the same or substantially the same properties and perform the same or substantially the same function as the original sequence. The term encompass polymers of any length, preferably polymers containing from about 2 to 1000 amino acids, more preferably from about 5 to 500 amino acids. The term includes amino acid polymers that are synthesized and that are isolated and purified from natural sources.

The term "probe" means (1) an oligonucleotide or polynucleotide, either RNA or DNA, whether occurring naturally as in a purified restriction enzyme digest or produced synthetically, that is capable of annealing with or specifically hybridizing to a polynucleotide with sequences complementary to the probe or (2) a peptide or polypeptide capable of specifically binding a particular protein or protein fragment to the substantial exclusion of other proteins or protein fragments. An oligonucleotide or polynucleotide probe may be either single or double stranded. The exact length of the probe will depend upon many factors, including temperature, source, and use. For example, for diagnostic applications, depending on the complexity of the target sequence, an oligonucleotide probe typically contains about 10 to 100, 15 to 50, or 15 to 25 nucleotides. In certain diagnostic applications, a polynucleotide probe contains about 100-1000, 300-600, nucleotides, preferably about 300 nucleotides. The probes herein are selected to be "substantially" complementary to different strands of a particular target sequence. This means that the probes must be sufficiently complementary to specifically hybridize or anneal with their respective target sequences under a set of predetermined conditions. Therefore, the probe sequence need not reflect the exact complementary sequence of the target. For example, a noncomplementary nucleotide fragment may be attached to the 5' or 3' end of the probe, with the remainder of the probe sequence being complementary to the target sequence. Alternatively, noncomplementary bases or longer sequences can be interspersed into the probe provided that the probe sequence has sufficient complementarity with the sequence of the target polynucleotide to specifically anneal to the target polynucleotide. A peptide or polypeptide probe may be any molecule to which the protein or peptide specifically binds, including DNA (for DNA binding proteins), antibodies, cell membrane receptors, peptides, cofactors, lectins, sugars, polysaccharides, cells, cell membranes, organelles and organellar membranes.

The terms "sample" and "specimen" mean any animal tissue or fluid containing polynucleotides, including cells and other tissue containing DNA and RNA. Examples include: blood, kidney, connective, epithelial, lymphoid, muscle, nervous, sputum, and the like. A sample may be solid or liquid and that may contain DNA, RNA, cDNA, for example, bodily fluids such as blood or urine, cells, cell preparations or soluble fractions or media aliquots thereof, chromosomes, organelles, and the like.

The term "specifically bind" means a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

The term "specifically hybridize" means an association between two single stranded polynucleotides of sufficiently complementary sequence to permit such hybridization under predetermined conditions generally used in the art (sometimes termed "substantially complementary"). For example, the term may refer to hybridization of a polynucleotide probe with a substantially complementary sequence contained within a single stranded DNA or RNA molecule according to an aspect of the invention, to the substantial exclusion of hybridization of the polynucleotide probe with single stranded polynucleotides of non-complementary sequence.

The term "stringent conditions" means (1) hybridization in 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C., (2) hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 mg/ml), 0.1% SDS, and 10% dextran sulfate at 42° C.; with washes at 42° C. in 0.2×SSC and 0.1% SDS or washes with 0.015 M NaCl, 0.0015 M sodium citrate, 0.1% Na2SO4 at 50° C. or similar art-recognized procedures employing similar low ionic strength and high temperature washing agents and similar denaturing agents.

The term "useful variations" means (1) for a polynucleotide, the complements of the polynucleotide; the homologs of the polynucleotide and its complements; the variants of the polynucleotide, its complements, and its homologs; and the fragments of the polynucleotide, its complements, its homologs, and its variants and (2) for a polypeptide, the homologs of the polypeptide; the variants of the polypeptide and its homologs; and the fragments of the polynucleotide, its homologs, and its variants.

The term "variant" means (1) a polynucleotide sequence containing any substitution, variation, modification, replacement, deletion, or addition of one or more nucleotides from or to a polynucleotide sequence and that has the same or substantially the same properties and performs the same or substantially the same function as the original sequence and (2) a polypeptide sequence containing any substitution, variation, modification, replacement, deletion, or addition of one or more amino acids from or to a polypeptide sequence and that has the same or substantially the same properties and performs the same or substantially the same function as the original sequence. The term therefore includes single nucleotide polymorphisms (SNPs) and allelic variants and includes conservative and non-conservative amino acid substitutions in polypeptides. The term also encompasses chemical derivatization of a polynucleotide or polypeptide and substitution of nucleotides or amino acids with nucleotides or amino acids that do not occur naturally, as appropriate.

Unless defined otherwise, all technical and scientific terms and any acronyms used herein have the same meanings as commonly understood by one of ordinary skill in the art in the field of the invention.

Probes

The probes useful in the practice of the invention and which are utilized in the identification of the feline biomarkers in the feline samples comprise SEQ ID NOS: 1 to 8. The probe sequences correspond to the following probe identification numbers used in the proprietary feline gene chip manufactured by Affymetrix, identified as Affymetrix Feline GeneChip®, as more fully described in this specification.

HP04719_at corresponds to SEQ ID NO. 1, which is useful in hybridizing to a feline homolog of the mRNA sequence of the canine gene *Canis lupus familiaris* mRNA for putative secreted frizzled-related protein 2 (sfrp2 gene). The sequence for the feline homolog to which SEQ ID NO. 1 hybridizes is SEQ ID. NO. 9. The Probe ID No. corresponds to the ID number used on the Affymetrix Feline GeneChip®. The corresponding canine mRNA sequence is identified by Accession No. NM_001002987.1 at GeneID: 475471.

HP12767_at corresponds to SEQ ID NO. 2, which is useful in hybridizing to the feline homolog of the mRNA sequence of *Canis familiaris* similar to retinol binding protein 5; cellular; transcript variant 2. The sequence for the feline homolog to which SEQ ID NO. 2 hybridizes is SEQ ID. NO. 10. The Probe ID No. corresponds to the ID number used on the Affymetrix Feline GeneChip®. The corresponding canine mRNA sequence is identified by LOC477706 and by NCBI reference sequence: XM_848184.1.

HP04078_at corresponds to SEQ ID NO. 3, which is useful in hybridizing to the feline homolog of the mRNA sequence of gene *Canis familiaris* similar to Lumican precursor (Keratan suitable proteoglycan lumican) (KSPG lumican). The corresponding canine sequence is identified by LOC 482599). The corresponding canine mRNA sequence is identified by NCBI reference sequence: XM_539716.2 at GeneID: 482599.

HP04079_at corresponds to SEQ ID NO. 4, which is useful in hybridizing to the feline homolog of the mRNA sequence of *Canis lupus familiaris* decorin (DCN). The corresponding canine mRNA sequence is identified as NCBI reference sequence: NM_001003228.1 at GeneID: 403904.

HP06873_at corresponds to SEQ ID NO. 5, which is useful in hybridizing to the feline homolog of the mRNA sequence of *Equus caballus* similar to collagen; type III; alpha 1 (Ehlers-Danlos syndrome type IV; autosomal dominant. The corresponding equine mRNA sequence is identified by NCBI reference sequence: XM_001917620 at GeneID 100034123.

HP00944_at corresponds to SEQ ID NO. 6, which is useful in hybridizing to the feline homolog of the mRNA sequence of *Canis familiaris* matrix metalloproteinase-2 (MMP-2). The corresponding canine mRNA sequence is identified by NCBI reference sequence: XM_535300.2 at GeneID: 403733.

HP09664_at corresponds to SEQ ID NO. 7, which is useful in hybridizing to the feline mRNA sequence of synthetic construct *Felis domesticus* PUMP-1 mRNA. Feline PUMP-1 is identified as Accession No. U04444.1.

HP00012_at corresponds to SEQ ID NO. 8, which is useful in hybridizing to the feline homolog of the mRNA sequence of Predicted: *Macaca mulatta* matrix metalloproteinase 19; transcript variant 1 (MMP19). The NCBI reference sequence number is XM_001111542 at GeneID 7100111.

Biomarkers

The biomarkers useful in the practice of the present invention are: secreted frizzled-related protein 2 (sFRP2); retinol binding protein 5 (rbp5); lumican (LUM); decorin (DCN); collagen alpha 1 (III) chain, variant 12 (COL3A1); and matrix metalloproteinase-2, -7 and -19 (MMP2, MMP7 and MMP19), as more fully described below and in the sequence listings appended to this specification.

SEQ ID NO. 9 corresponds to a feline nucleic acid sequence homologous to *Canis lupus familiaris* secreted frizzled-related protein 2 mRNA. The canine sequence is identified by NCBI reference sequence: NM_001002987.1 and GeneID: 475471. The full length canine nucleotide sequence is 1760 bp. The corresponding canine polypeptide has NCBI reference sequence NP_001002987.1. Canine secreted frizzled-related protein 2 (sFRP2) is a 294 amino acid. Members of the 'frizzled' (FZ) transmembrane protein family are receptors for Wnt family members, cysteine-rich glycosylated ligands implicated in a variety of cellular processes, including control of cell polarity and malignant transformation. The secreted frizzled-related proteins (sFRPs) appear to act as soluble modulators of Wnt signaling by competing with membrane-bound frizzled receptors for the binding of secreted Wnt ligands.

SEQ ID NO. 10 corresponds to a feline nucleic acid sequence homologous to *Canis familiaris* similar to retinol binding protein 5, cellular, transcript variant 2 (LOC477706) mRNA. The canine sequence is identified by NCBI reference sequence XM_848184.1. The full length canine nucleotide sequence is 511 bp. The corresponding canine polypeptide has NCBI reference sequence XP_853277.1. Canine rbp5 is a 135 amino acid protein. Rbp5 belongs to the lipocalin family and is believed to be a carrier for retinol (vitamin A alcohol) intracellularly.

SEQ ID NO. 11 corresponds to a feline nucleic acid sequence homologous to Predicted: *Canis familiaris* similar to lumican precursor (keratan sulfate proteoglycan lumican) (LOC 482599) mRNA. The canine sequence is identified by NCBI reference sequence XM_539716.2 The full length canine nucleotide sequence is 2028 bp. The corresponding canine polypeptide has NCBI reference sequence XP_539716.1 Canine lumican precursor (keratan sulfate proteoglycan lumican) is a 338 amino acid protein. Lumican (LUM) is an extracellular matrix sulfated proteoglycan that interacts with proteins that are involved in matrix assembly such as collagen type I and type VI. LUM is involved in cell proliferation and tissue morphogenesis. Lumican is thought to play an important role in the regulation of collagen fiber assembly. The protein is also a binding partner of TGF-beta.

SEQ ID NO. 12 corresponds to a feline nucleic acid sequence homologous to *Canis lupus familiaris* decorin precursor, mRNA. The sequence is identified by NCBI reference sequence NM_001003228.1 at GeneID 403904. The full length canine nucleotide sequence is 1470 bp. The corresponding canine polypeptide sequence has NCBI reference sequence: NM_001003228.1. The corresponding canine polypeptide canine decorin precursor has NCBI reference sequence NP_001003228.1. Canine decorin precursor is a 360 amino acid protein. The protein is a small cellular or pericellular matrix proteoglycan closely related in structure to biglycan protein and is a component of connective tissue. Decorin binds to type I collagen fibrils, and plays a role in matrix assembly. It contains one attached glycosaminoglycan chain. This protein is believed to be capable of suppressing the growth of various tumor cell lines. A number of alternatively spliced transcript variants have been identified in the scientific literature for this gene.

SEQ ID NO. 13 corresponds to a feline nucleic acid sequence homologous to *Equus caballus* collagen, type III, alpha 1 (Ehlers Danlos syndrome type IV, autosomal dominant) (COL3A1), mRNA. The sequence is identified by NCBI reference sequence XM_001917620.1 at GeneID 100034123. The full length equine nucleotide sequence is 5492 bp. The corresponding equine polypeptide sequence has NCBI reference sequence: XP_001917655. Equine collagen, type III, alpha 1 (Ehlers Danlos syndrome type IV, autosomal dominant) (COL3A1) is a 1466 amino acid protein. Type III collagen in humans is a fibrillar-forming collagen comprising 3 alpha-1(III) chains and is expressed in early embryos and throughout embryogenesis. In the adult, type III collagen is a major component of the extracellular matrix in a variety of internal organs and skin. Mutations in the COL3A1 gene, which encodes type III procollagen, cause type IV Ehlers-Danlos syndrome, a disease leading to aortic rupture in early adult life.

SEQ ID NO. 14 corresponds to a feline nucleic acid sequence homologous to *Canis familiaris* matrix metalloproteinase-2 (MMP-2), mRNA. The sequence is identified by NCBI reference sequence XM_535300.2 at GeneID 4037333. The full length canine nucleotide sequence is 2618 bp. The corresponding equine polypeptide sequence has NCBI reference sequence: XP_535300.2. Canine MMP-2 is a 612 amino acid protein. This type IV collagenase is a member of a group of secreted zinc metalloproteases which, in mammals, degrade the collagens of the extracellular matrix. MMP2 has three repeats of fibronectin type II domains inserted in the catalytic domain; see the minireview of matrix metalloproteinases provided by Nagase et al., J. Biol. Chem., 1999, Vol. 274(31): 21491-21494.

SEQ ID NO. 15 corresponds to a feline nucleic acid sequence for *Felis domesticus* PUMP-1 mRNA, partial cds. The sequence is identified as NCBI reference sequence FDU04444 at GeneBank: U04444.1. The full length feline PUMP-1 nucleotide sequence is 1001 bp. The full length PUMP-1 polypeptide sequence is identified as GeneBank sequence: AAA18222.1. Feline PUMP-1 is a 262 amino acid protein.

SEQ ID NO 16 corresponds to a feline nucleic acid sequence homologous to Predicted: *Macaca mulatta* matrix metalloproteinase 19, transcript variant 1 (MMP-19), mRNA. The rhesus monkey sequence is identified as NCBI reference sequence: XM_001111542.1. The full length rhesus monkey nucleotide sequence is 2182 bp. The full length polypeptide sequence is identified as XP_001111542.1. The rhesus monkey MMP-19 is a 485 amino acid protein.

It is to be understood in relation to the discussion of embodiments of the invention that the present invention additionally contemplates combinations of biomarkers comprising genes and their expression products that are selected from the group consisting of: secreted frizzle-related protein-2 (SFRP2) or a feline homolog or fragment thereof (SEQ ID NO. 9); retinol binding protein 5 (rbp5) or a feline homolog or fragment thereof (SEQ ID No. 10); lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16). Embodiments of the invention contemplate constructing panels of biomarkers from various combinations of the two groupings of genes and their expression products.

In a certain embodiments of the present invention, the feline may have normal kidney function, as defined by art-recognized clinical measurements, e.g., glomerular filtration rate, creatinine clearance, urinary protein levels, blood creatinine levels, urinary creatinine levels and/or blood urea nitrogen levels, and the methods of the invention may be used to predict, detect and diagnose in such feline a change from a normal state to an abnormal state leading to a kidney disorder characterized by reduced renal function, renal failure, reduced glomerular filtration rate and glomerulonephritis.

In another preferred embodiment, the method of the invention can be practiced by using an array that detects gene expression changes, or the level or activity of one or more genes, or their expression products, selected from the group consisting of: secreted frizzle-related protein-2 (SFRP2) or a feline homolog or fragment thereof (SEQ ID NO. 9); retinol binding protein 5 (rbp5) or a feline homolog or fragment thereof (SEQ ID No. 10); lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16). In one method, such array is a DNA microarray. The level of activity or expression of one or more genes may be determined by measuring the expression product of such genes which may be a polynucleotide or a polypeptide or protein.

In another preferred embodiment, the method of the invention can be practiced by using an array that detects gene expression changes, or the level or activity of one or more genes, or their expression products, selected from the group consisting of: secreted frizzle-related protein-2 (SFRP2) or a feline homolog or fragment thereof (SEQ ID NO. 9) and retinol binding protein 5 (rbp5) or a feline homolog or fragment thereof (SEQ ID No. 10); and, optionally, a second group of at least one polynucleotide selected from the group consisting of: lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ II) No. 16). In one method, such array is a DNA microarray. The level of activity or expression of one or more genes may be determined by measuring the expression product of such genes which may be a polynucleotide or a polypeptide or protein.

In one aspect the invention includes contacting a tissue sample or bodily fluid specimen with an agent that detects in a feline one or more genes or the expression product of such one or more genes selected from the group consisting of: secreted frizzle-related protein-2 (SFRP2) or a feline homolog or fragment thereof (SEQ ID NO. 9); retinol binding protein 5 (rbp5) or a feline homolog or fragment thereof (SEQ ID No. 10); lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16). The agent can be an antibody or a nucleic acid probe used in conjunction with conventional assay means such as immobilization on a solid phase, microtiter wells, tubes, dipsticks or other conventional means.

In another aspect the invention includes contacting a tissue sample or bodily fluid specimen with an agent that detects in a feline one or more genes or the expression product of such one or more genes selected from the group consisting of: secreted frizzle-related protein-2 (SFRP2) or a feline homolog or fragment thereof (SEQ ID NO. 9) and retinol binding protein 5 (rbp5) or a feline homolog or fragment thereof (SEQ ID No. 10); and, optionally, a second group of at least one polynucleotide selected from the group consisting of: lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16). The agent can be an antibody or a nucleic acid probe used in conjunction with conventional assay means such as immobilization on a solid phase, microtiter wells, tubes, dipsticks or other conventional means.

Another embodiment of the method of the invention encompasses use of conventional assay means to determine gene expression in a feline either alone or in conjunction with gene expression array displays employing polypeptides and/or polynucleotides, such conventional assay means comprising one or more of ELISA, RIA, immunoblot assays, in situ hybridization, Northern blot analysis, Western blot analysis and Luminex X-Map® analysis.

A further aspect of the invention is that it relates to the identification of novel biomarkers of a kidney disorder in felines as well as methods of detection of a kidney disorder in such felines based on a characteristic pattern of gene expression of such biomarkers in vivo. Specifically, the methods of the invention comprise detecting differential expression, compared to a control expression level, of at least one biomarker, in a body sample, preferably a blood sample, wherein the detection of differential expression of such biomarker specifically identifies felines that have glomerulonephritis. Thus, such methods rely upon the detection of at least one biomarker that is differentially expressed in a feline having a kidney disorder in comparison to cells from normal or control animals. The biomarkers of the invention are proteins and/or nucleic acids that are differentially expressed in a feline having or likely to develop an abnormal kidney disorder, in particular a kidney disorder. In one embodiment the gene expression pattern comprises at least one RNA transcript or its translation product selected from a group of at least one gene or the translation product of such gene selected from the group consisting of: secreted frizzle-related protein-2 (SFRP2) or a feline homolog or fragment thereof (SEQ ID NO. 9); retinol binding protein 5 (rbp5) or a feline homolog or fragment thereof (SEQ ID No. 10); lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16). In a preferred embodiment, the differential is at least about one standard deviation around the mean. In a more preferred embodiment, the differential is at least about a 2-fold differential.

A further aspect of the invention is that it relates to the identification of novel biomarkers of a kidney disorder in felines as well as methods of detection of a kidney disorder in such felines based on a characteristic pattern of gene expression of such biomarkers in vivo. Specifically, the methods of the invention comprise detecting differential expression, compared to a control expression level, of at least one biomarker, in a body sample, preferably a blood sample, wherein the detection of differential expression of such biomarker specifically identifies felines that have glomerulonephritis. Thus, such methods rely upon the detection of at least one biomarker that is differentially expressed in a feline having a kidney disorder in comparison to cells from normal or control animals. The biomarkers of the invention are proteins and/or nucleic acids that are differentially expressed in a feline having or likely to develop an abnormal kidney disorder, in particular a kidney disorder. In one embodiment the gene expression pattern comprises at least one RNA transcript or its translation product selected from a first group of at least one gene or the translation product of such gene selected from the group consisting of: secreted frizzle-related protein-2 (SFRP2) or a feline homolog or fragment thereof (SEQ ID NO. 9) and retinol binding protein 5 (rbp5) or a feline homolog or fragment thereof (SEQ ID No. 10); and, optionally, a second group of at least one polynucleotide selected from the group consisting of: lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16). In a preferred embodiment, the differential is at least about one standard deviation around the mean. In a more preferred embodiment, the differential is at least about a 2-fold differential.

Yet a further aspect of the invention relates to: biomarkers of glomerulonephritis in felines comprising at least one RNA transcript or its translation product selected from the group consisting of: secreted frizzle-related protein-2 (SFRP2) or a feline homolog or fragment thereof (SEQ ID NO. 9); retinol binding protein 5 (rbp5) or a feline homolog or fragment thereof (SEQ ID No. 10); lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16). In another embodiment the biomarker or biomarkers are used to detect glomerulonephritis. In a preferred embodiment, the foregoing biomarker or biomarkers are used to differentiate stages of glomerulonephritis in a feline.

Yet a further aspect of the invention relates to: biomarkers of glomerulonephritis in felines comprising at least one RNA transcript or its translation product selected from the group consisting of: secreted frizzle-related protein-2 (SFRP2) or a feline homolog or fragment thereof (SEQ ID NO. 9) and retinol binding protein 5 (rbp5) or a feline homolog or fragment thereof (SEQ ID No. 10); and, optionally, a second group of at least one polynucleotide selected from the group consisting of: lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16). In another embodiment the biomarker or biomarkers are used to detect glomerulonephritis. In a preferred embodiment, the foregoing biomarker or biomarkers are used to differentiate stages of glomerulonephritis in a feline.

In a further aspect, the invention relates to compositions comprising one or more nucleic acid probes that specifically hybridize to a nucleic acid, or fragment thereof, encoding a biomarker of the present invention selected from the group consisting of: secreted frizzle-related protein-2 (SFRP2) or a feline homolog or fragment thereof (SEQ ID NO. 9); retinol binding protein 5 (rbp5) or a feline homolog or fragment thereof (SEQ ID No. 10); lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16).

In a further aspect, the invention relates to compositions comprising one or more nucleic acid probes that specifically hybridize to a nucleic acid, or fragment thereof, encoding a biomarker of the present invention selected from the group consisting of: secreted frizzle-related protein-2 (SFRP2) or a feline homolog or fragment thereof (SEQ ID NO. 9) and retinol binding protein 5 (rbp5) or a feline homolog or fragment thereof (SEQ ID No. 10); and, optionally, a second group of at least one polynucleotide selected from the group consisting of: lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16).

In an additional aspect, the invention relates to compositions comprising antibodies that specifically bind to a polypeptide encoded by a gene expressing a biomarker of the present invention selected from the group consisting of: secreted frizzle-related protein-2 (SFRP2) or a feline homolog or fragment thereof (SEQ ID NO. 9); retinol binding protein 5 (rbp5) or a feline homolog or fragment thereof (SEQ ID No. 10); lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ II) No. 15); and matrix metalloproteinase-19 (MMP19) or a feline homolog or fragment thereof (SEQ ID No. 16).

In an additional aspect, the invention relates to compositions comprising antibodies that specifically bind to a polypeptide encoded by a gene expressing a biomarker of the present invention selected from the group consisting of: secreted frizzle-related protein-2 (SFRP2) or a feline homolog or fragment thereof (SEQ ID NO. 9) and retinol binding protein 5 (rbp5) or a feline homolog or fragment thereof (SEQ ID No. 10); and, optionally, a second group of at least one polynucleotide selected from the group consisting of: lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16).

It is further contemplated herein that the methods of the present invention may be used in combination with traditional diagnostic techniques that are able to detect the physical and morphological characteristics of kidney disorders. Thus, for example, the characterization of differential expression in genes for kidney in cells obtained from a tissue samples or bodily fluid specimens of a feline may be combined with conventional diagnostic (e.g., radiological) techniques in order to corroborate a diagnosis of a kidney disorder in a feline, including, for example, glomerulonephritis.

A further aspect of the invention is a method for diagnosis and/or prognosis of kidney disorder in a feline, wherein the method comprises the steps of: obtaining at least one tissue sample or bodily fluid specimen from the animal; determining the amount of one or more biomarkers selected from Table 3 in said at least one sample or specimen obtained from the animal, wherein said biomarker is a polypeptide, protein, RNA, DNA, polynucleotide or metabolite thereof.

Yet another embodiment of the invention is a kit for diagnosis and/or prognosis of a kidney disorder in a feline, particularly for carrying out the method for diagnosis and/or prognosis of glomerulonephritis in a feline wherein the method comprises the steps of: obtaining at least one tissue sample or bodily fluid specimen from the animal; determining the amount of one or more biomarkers selected from Table 3 in said at least one sample or specimen obtained from the animal, wherein said biomarker is a polypeptide, protein, RNA, DNA, polynucleotide or metabolite thereof, and optionally, further comprising a detectable agent linked to said biomarker.

A still further embodiment of the invention is a reagent for diagnosis and/or prognosis of glomerulonephritis in a feline particularly for carrying out the method for diagnosis and/or prognosis of glomerulonephritis in a feline, wherein the method comprises the steps of: obtaining at least one tissue sample or bodily fluid specimen from the animal; determining the amount of one or more biomarkers selected from Table 3 in said at least one sample or specimen obtained from a feline, wherein said biomarker is a polypeptide, protein, RNA, DNA, polynucleotide or metabolite thereof, and optionally further comprising a detectable agent linked to said biomarker.

A further aspect of the invention is a method for diagnosis and/or prognosis of kidney disorder in a feline, wherein the method comprises the steps of: obtaining at least one tissue sample or bodily fluid specimen from the animal; determining the amount of one or more biomarkers selected from Tables 3 and 4 in said at least one sample or specimen obtained from the animal, wherein said biomarker is a polypeptide, protein, RNA, DNA, polynucleotide or metabolite thereof.

Yet another embodiment of the invention is a kit for diagnosis and/or prognosis of a kidney disorder in a feline, particularly for carrying out the method for diagnosis and/or prognosis of glomerulonephritis in a feline wherein the method comprises the steps of: obtaining at least one tissue sample or bodily fluid specimen from the animal; determining the amount of one or more biomarkers selected from Tables 3 and 4 in said at least one sample or specimen obtained from the animal, wherein said biomarker is a polypeptide, protein, RNA, DNA, polynucleotide or metabolite thereof, and optionally, further comprising a detectable agent linked to said biomarker.

A still further embodiment of the invention is a reagent for diagnosis and/or prognosis of glomerulonephritis in a feline particularly for carrying out the method for diagnosis and/or prognosis of glomerulonephritis in a feline, wherein the method comprises the steps of: obtaining at least one tissue sample or bodily fluid specimen from the animal; determining the amount of one or more biomarkers selected from Tables 3 and 4 in said at least one sample or specimen obtained from a feline, wherein said biomarker is a polypeptide, protein, RNA, DNA, polynucleotide or metabolite thereof, and optionally, further comprising a detectable agent linked to said biomarker.

Another embodiment of the invention is the use of one or more polypeptides, proteins, RNAs, DNAs, polynucleotides or metabolites thereof selected from the group consisting of: secreted frizzle-related protein-2 (SFRP2) or a feline homolog or fragment thereof (SEQ ID NO. 9); retinol binding protein 5 (rbp5) or a feline homolog or fragment thereof (SEQ ID No. 10); lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16) as a biomarker for diagnosis and/or prognosis of glomerulonephritis, particularly for forming a kit for diagnosis or prognosis of glomerulonephritis in a feline.

Another embodiment of the invention is the use of one or more polypeptides, proteins, RNAs, DNAs, polynucleotides or metabolites thereof selected from the group consisting of: secreted frizzle-related protein-2 (SFRP2) or a feline homolog or fragment thereof (SEQ ID NO. 9) and retinol binding protein 5 (rbp5) or a feline homolog or fragment thereof (SEQ ID No. 10); and, optionally, a second group of at least one polynucleotide selected from the group consisting of: lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16) as a biomarker for diagnosis and/or prognosis of glomerulonephritis, particularly for forming a kit for diagnosis or prognosis of glomerulonephritis in a feline.

Another embodiment of the invention is the use of one or more polypeptides, proteins, RNAs, DNAs, polynucleotides or metabolites thereof selected from the group consisting of: secreted frizzle-related protein-2 (SFRP2) or a feline homolog or fragment thereof (SEQ ID NO. 9); retinol binding protein 5 (rbp5) or a feline homolog or fragment thereof (SEQ ID No. 10); lumican (LUM) or a feline homolog or fragment thereof (SEQ ID No. 111); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16) as a biomarker for diagnosis and/or prognosis of a kidney disorder, particularly for forming a kit for diagnosis or prognosis of a kidney disorder in a feline.

Another embodiment of the invention is the use of one or more polypeptides, proteins, RNAs, DNAs, polynucleotides or metabolites thereof selected from the group consisting of: secreted frizzle-related protein-2 (SFRP2) or a feline homolog or fragment thereof (SEQ ID NO. 9) and retinol binding protein 5 (rbp5) or a feline homolog or fragment thereof (SEQ II) No. 10); and, optionally, a second group of at least one polynucleotide selected from the group consisting of: lumican (LUM) or a feline homolog or fragment thereof (SEQ ID No. 11); decorin (DCN) or a feline homolog or fragment thereof (SEQ ID No. 12); collagen alpha 1 (III) chain, variant 12 (COL3A1) or a feline homolog or fragment thereof (SEQ ID No. 13); matrix metalloproteinase-2 (MMP2) or a feline homolog or fragment thereof (SEQ ID No. 14); matrix metalloproteinase-7 (MMP7, PUMP-1) or a feline homolog or fragment thereof (SEQ ID No. 15); and matrix metalloproteinase-19 (MMP19) or a feline homolog or fragment thereof (SEQ ID No. 16) as a biomarker for diagnosis and/or prognosis of a kidney disorder, particularly for forming a kit for diagnosis or prognosis of a kidney disorder in a feline.

Yet another embodiment is such kit, wherein the reagents and equipment comprise DNA microarray analysis materials including oligonucleotide microarray, cDNA microarray, and focused gene chip, or a combination thereof.

Other and further objects, features, and advantages of the present invention will be readily apparent to those skilled in the art.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 5 should be considered to have specifically disclosed subranges such as from 1 to 3, from 1 to 4, from 2 to 4, from 2 to 5, from 3 to 5 etc., as well as individual numbers within that range, for example, 1, 2, 3, 4, and 5. This applies regardless of the breadth of the range The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as: Genome Analysis: A Laboratory Manual Series (Vols. I-IV); Using Antibodies: A Laboratory Manual; Cells: A Laboratory Manual; PCR Primer: A Laboratory Manual, and Molecular Cloning: A Laboratory Manual (all from Cold Spring Harbor Laboratory Press); Stryer, L. (1995) Biochemistry (4th Ed.) Freeman, New York; Gait, "Oligonucleotide Synthesis: A Practical Approach" 1984, IRL Press, London, Nelson and Cox (2000); Lehninger, Principles of Biochemistry 3rd Ed., W.H. Freeman Pub., New York, N.Y.; and Berg et al. (2002) Biochemistry, 5th Ed., W.H. Freeman Pub., New York, N.Y., all of which are herein incorporated in their entirety by reference for all purposes.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248, 6,309,822 and 6,344,316. Genotyping and uses therefore are shown in U.S. Ser. No. 60/319,253, 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

Those skilled in the art will recognize that the products and methods embodied in the present invention may be applied to a variety of systems, including commercially available gene expression monitoring systems involving nucleic acid probe arrays, membrane blots, microwells, beads and sample tubes, constructed with various materials using various methods known in the art. Accordingly, the present invention is not limited to any particular environment, and the following description of specific embodiments of the present invention is for illustrative purposes only.

The gene expression monitoring system, in a preferred embodiment, may comprise a nucleic acid probe array (including an oligonucleotide array, a cDNA array, a spotted array, and the like), membrane blot (such as used in hybridization analysis such as Northern, Southern, dot, and the like), or microwells, sample tubes, beads or fibers (or any solid support comprising bound nucleic acids). See U.S. Pat. Nos. 5,770,722, 5,744,305, 5,677,195, 5,445,934 and 6,040,193 which are incorporated herein by reference. The gene expression monitoring system may also comprise nucleic acid probes in solution.

The present invention also contemplates sample preparation involving amplification. A genomic sample may be amplified by a variety of mechanisms, some of which may employ PCR. See, e.g., PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159, 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517 and 6,063,603, each of which is incorporated herein by reference). Other amplification methods that may be used are described in, U.S. Pat. Nos. 5,242,794, 5,494,810, 4,988,617, 6,344,316 and in U.S. Ser. No. 09/854,317, each of which is incorporated herein by reference.

Additional methods of sample preparation and techniques are described in Dong et al., Genome Research 11, 1418 (2001), in U.S. Pat. Nos. 6,361,947, 6,391,592 and U.S. patent application Ser. Nos. 09/916,135, 09/920,491, 09/910, 292 and 10/013,598.

The gene expression monitoring system according to the present invention may be used to facilitate a comparative analysis of expression in different cells or tissues, different subpopulations of the same cells or tissues, different physiological states of the same cells or tissue, different developmental stages of the same cells or tissue, or different cell populations of the same tissue. In a preferred embodiment, the proportional amplification methods of the present invention can provide reproducible results (i.e., within statistically significant margins of error or degrees of confidence) sufficient to facilitate the measurement of quantitative as well as qualitative differences in the tested samples.

Polynucleotide hybridization assays are well known in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Methods and apparatus for carrying out repeated and controlled hybridization reactions have been described in U.S. Pat. Nos. 5,871,928, 5,874,219, 6,045,996, 6,386,749 and 6,391,623 each of which are incorporated herein by reference. Signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803 and 6,225,625, in U.S. Patent application 60/364,731 and in PCT Application PCT/US99/06097 (published as WO99/47964), each of which also is hereby incorporated by reference in its entirety for all purposes. Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

The invention is not limited to the particular methodology, protocols, and reagents described herein because they may vary. Further, the terminology used herein is for the purpose of describing particular embodiments only and is not intended to limit the scope of the present invention.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, is relevant prior art for the present invention and the right to challenge the accuracy and pertinence of such patents, patent applications, publications, and other references is specifically reserved.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

EXAMPLES

Example 1

Classification of Felines with Chronic Kidney Disease According to the Guidelines of the International Renal Interest Society In the Examples that follow, felines exhibiting clinical signs of chronic kidney disease were tested versus animals not exhibiting signs or symptoms of chronic kidney disease. Pathological diagnoses of chronic kidney disease were made based on the criteria set forth in Tables 1 and 2 below and in accordance with the guidelines of the International Renal Interest Society (IRIS).

Staging of chronic kidney disease (CKD) is undertaken following the diagnosis of CKD in order to facilitate appropriate treatment and monitoring of the subject animal. Staging is based initially on fasting plasma creatinine, assessed on at least two occasions in the stable animal. Felines demonstrating normal renal function and no clinical signs or symptoms of CKD were grouped as non-disease felines. Stage 1 in felines corresponds to prior classifications of early renal disease with no biochemical evidence of CKD to renal insufficiency, where no azotemia is detected, but where glomerular filtration rate (GFR) may be reduced and there may be a poor concentrating ability of the kidneys. Stage 2 corresponds to the prior classification of early renal failure. In Stage 2, mild azotemia is noted. Stage 3 corresponds to prior classification of uremic renal failure, where moderate azotemia is detected. Systemic signs of uremic renal failure may be present such as bone pain, uremic gastritis, anemia and metabolic acidosis. Stage 4 corresponds to end-stage renal failure, which is characterized by severe azotemia and increasing systemic clinical signs of uremic crisis.

Table 1 identifies the five categories of felines studied, respectively. A total of 42 felines diagnosed as not having CKD were studied. A total of 14 Stage 1 felines exhibited minimal glomerulonephritis (GN). The number of felines studied exhibiting advanced stages of CKD were: Stage 2 mild GN=24; Stage 3 moderate GN=8 and Stage 4 marked GN=13. Plasma creatinine levels for each of the groups of felines are shown in Table 2 as mean and median plasma creatinine levels for each group of felines.

TABLE 1

Staging for Felines

| IRIS CKD Staging | Plasma Creatinine range mg/dl |
|---|---|
| Non-Disease | <1.6 with no firm evidence of disease |
| Stage 1 | <1.6 (<140 μmol/l) with evidence of disease. Non-azotemic. Some other renal abnormality present (e.g. inadequate concentrating ability without identifiable non-renal cause; abnormal renal palpation and/or renal imagining findings; proteinuria of renal origin; abnormal renal biopsy |
| Stage 2 | 1.6 to 2.8 (140-249 μmol/l) Mild renal azotemia. Clinical signs usual mild or absent. |
| Stage 3 | 2.9 to 5.0 (250-439 μmol/l) Moderate renal azotemia. Many clinical signs may be present. |
| Stage 4 | >5.0 (>440 μmol/l) Severe renal azotemia. Many extra-renal clinical signs present. |

TABLE 2

Plasma Creatinine Levels

| Pathological Diagnosis | Mean Plasma Creatinine mg/dl | Median Plasma Creatinine mg/dl |
|---|---|---|
| Non-Disease (n = 15) | 1.3 | 1.0 |
| Minimal GN (n = 4) | 1.4 | 1.5 |

TABLE 2-continued

Plasma Creatinine Levels

| Pathological Diagnosis | Mean Plasma Creatinine mg/dl | Median Plasma Creatinine mg/dl |
|---|---|---|
| Mild GN (n = 10) | 2.4 | 1.8 |
| Moderate GN (n = 20) | 3.8 | 2.6 |
| Marked GN (n = 13) | 7.1 | 7.1 |

Example 2

Candidate Selection Criteria

In the examples that follow reporting on felines for which gene expression data was obtained by DNA microarray analysis, selection criteria were established in order to identify certain genes and expressed proteins as suitable biological markers of chronic kidney disease, and, correspondingly, glomerulonephritis. In order to be identified as a biologically meaningful marker of CKD, the gene expression profile was determined to require that: (1) the gene be an excreted protein; (2) there must be a differential expression level between normal animals evidencing no clinical signs or symptoms of glomerulonephritis and animals evidencing minimal, mild, moderate or marked (Stage 1 to 4, respectively) signs of CKD of at least 2-fold (up- or down-regulation); (3) the gene expression levels must correlate with disease progression from minimal to mild, moderate and marked (Stages 1 to 4); and (4) there is at least one standard deviation around the mean between non-disease animals and the moderate animals. The latter selection criterion is based on the observation that the microarray gene chips are semi-quantitative devices and that log scale robust multi-array analysis (RMA) is used for normalization of data.

A skilled worker can select among a number of algorithms for analyzing gene chip data. These include MASS statistical algorithm, probe logarithmic intensity error estimation (PLIER) and robust multi-chip analysis (RMA). Processing algorithms are discussed in detail in the following references: Li, C. Mo, 2001, Model-based analysis of oligonucleotide arrays: expression index computation and outlier detection, Proc. Acad. Sci., Vol. 98:31-36; Irizarry R. A. et al., Exploration, normalization and summaries of high density oligonucleotide array probe level data, Biostatistics, 2003, Vol. 4:249-264; Irizarry et al., Summaries of Affymetrix GeneChip probe level data, Nucleic Acid Res., 2003, Vol. 31(4): e15; and Fan, W., A et al., A class f models for analyzing GeneChip gene expression analysis array data, BMC Genomics, 2005, Vol. 16: 6-16; Zhou, L et al., An expression index for Affymetrix GeneChips based on the generalized logarithm, Bioinformatics, 2005, Vol. 21(21): 3983-3989 and Hein A. K. et al., BGX: a fully Bayesian integrated approach to the analysis of Affymetrix GeneChip data, Biostatistics, 2005, Vol. 6: 349-373.

The raw data in the following examples was analyzed using GeneSpring version 7.0 (GS) software (Agilent Corporation) and validated using the R-Bioconductor (RB) freeware. Both software packages are used to compute probe intensities from the CEL files generated by the Affymetrix Instrument. The Present/Absent/Marginal calls per probe and P-values are computed using the R-Bioconductor and GeneSpring software separately.

The gene expression data is determined to be either "up" or "down"-regulated for any given analysis. The decision on whether a gene is "up" or "down" is based on the fold change, which is calculated as treatment intensity/control intensity for each individual probe. The fold change is considered down-regulated if its value is <½ and is upregulated if it is >2.0. Also, a probe is considered significant for further scrutiny if it is called as present in only one of the conditions being compared (treatment or control) and is "absent" or "marginal" in the other and the fold change is significant according to the software used.

Example 3

RNA Isolation Procedures

Materials and Methods. The following general procedures may be used to isolate RNA from tissue samples of felines and felines for gene expression profiling utilizing gene chips as further described in the Examples of this specification. It will be apparent to a person of ordinary skill in the art that these procedures or modifications thereof, as recognized within the art, can be applied to isolate RNA from tissue or body fluid samples for further gene expression analysis using a variety of analytical procedures available to a person of ordinary skill in the art, in particular microarray technologies.

Isolation of Ribonucleic Acid (RNA) from Tissue. Tissue samples may be collected, frozen in liquid nitrogen, thawed and then, ground in a mortal and pestle, homogenized and transferred to a 50 ml conical flask. The homogenized tissue sample is then processed using a TRIzol® RNA extraction method according to the manufacturer's instructions (Invitrogen) to produce good quality RNA which is then subjected to further genomic analysis.

Materials: ice, liquid nitrogen, frozen feline tissue, TRIzol® lysis reagent, chloroform minimum 99%, isopropyl alcohol, 70% ethanol (prepared with ethanol, absolute and deionized, RNase-free water), RNase Zap®, deionized water, RNA Storage Solution®, from Ambion.

Equipment: Ultra-Turrax T25 Power Homogenizer, Beckman Coulter Allegra 25R Centrifuge, Eppendorf Centrifuge, forceps, scalpel, hard cutting surface, i.e. cutting board, 1.5 mL DNase and RNase free/sterile microcentrifuge tubes, 50 mL DNase and RNase free/sterile disposable polypropylene tubes, P1000, P200, P20, P10 and P2 Rainin Pipetman pipettes, filter pipette tips for P1000, P200, P20, P10 and P2 pipettes, DNase and RNase free/sterile, and lint free wipes.

Preparations: Prepare 50 mL polypropylene tubes with 4 mL TRIzol® (one tube for each tissue selected for RNA isolation).

Tissue Homogenization: Fill a container capable of holding liquid nitrogen with 3-4 scoops of liquid nitrogen. Place a piece of frozen tissue immediately into the aforementioned container (the tissue should be about the size of a pea) and place the tissue into the appropriate labeled 50 mL polypropylene tube (that already contains 4 mL TRIzol®). Immediately begin homogenization using the Ultra-Turrax T25 Power Homogenizer. Homogenize on the highest setting (6) for 10-15 seconds. Cool the sample on ice for another 10-15 seconds and then repeat. Continue until the tissue is fully homogenized and the solution is cloudy. Upon complete homogenization, cap the 50 mL tube and return to the ice. Incubate the homogenized tissues at room temperature for 5 minutes before proceeding with the isolation procedure.

Example 4

RNA Preparation Procedures

RNA Isolation: The procedures given in the Invitrogen instructions provided with the TRIzol® reagent are generally followed. Separate the homogenized sample into four 1 mL aliquots in four 1.5 mL microcentrifuge tubes. Add 200 uL of chloroform to each 1 mL aliquot. Cap the tubes, vortex for 15 seconds and then shake up and down. The result should be a pink milky liquid. Incubate the tubes at room temperature for 2-3 minutes. Centrifuge the tubes for 15 minutes at 14,000 rpm and 4° C. Transfer the aqueous phase (top layer) to a sterile 1.5 mL microcentrifuge tube. The typical volume of the aqueous phase which should be transferred to the new tube is about 500 uL. Be sure not to transfer any of the intermediate or lower phases. Precipitate the RNA from solution by adding 500 uL of Isopropyl Alcohol to each microcentrifuge tube containing the aqueous layer. Shake the tubes up and down for at least 20 seconds. Incubate the samples at room temperature for 10 minutes. Centrifuge the samples for 10 minutes, 14,000 rpm at 4° C. Remove the supernatant carefully by aspirating off the liquid being sure not to lose the pellet. Add 1 mL of 70% ethanol to wash the pellet. Dislodge the pellet by flicking the tube (or tapping the tube on the bench top) and shake to mix. Centrifuge for 5 minutes, 8,200 rpm at 4° C. Remove the supernatant carefully by aspirating off the liquid being sure not to lose the pellet. Using a lint free wipe to carefully soak up excess ethanol to make sure the pellet is dry. Resuspend each pellet into 30 uL of RNA Storage Solution. Mix gently by pipetting until the RNA goes back into solution and then store at −80° C. It may be necessary to vortex the sample for a few seconds at a low speed to facilitate the resuspension of the RNA. If this is necessary, spin down the samples, using the microcentrifuge, prior to freezing.

RNA Cleaning: The procedures given in the RNeasy® Mini Handbook are followed.

RNA Isolation from Cells Cultured in OptiCell Chambers Using the RNeasy Mini Kit. Cells cultured from mammalian cell lines are used to isolate good quality RNA which is then used for future downstream genomic analysis. All work related to the culturing of the cells is to be done under strict aseptic conditions.

Reagents: 10×PBS, deionized $H_2O$, absolute ethanol, RNA Storage Solution, β-Mercaptoethanol, RNase Zap®, Buffer RLT, and Buffer RWI and Buffer RPE (provided in the RNeasy Mini Kit).

Equipment/Materials: RNeasy Mini Kit, QIAshredder spin columns, OptiCell knife, 20 mL sterile syringe, OptiCell tips, Cell scraper, P1000 Pipetman pipette, Rainin, P200 Pipetman pipette, Rainin, 100-100 uL filtered pipette tips, 1-200 uL filtered pipette tips, sterile transfer pipettes, 55 mL sterile solution basin, 1.5 mL sterile microcentrifuge tubes, and Eppendorf Microcentrifuge.

Solutions: Buffer RLT (stock provided in RNeasy Mini Kit); —Add 100 uL of β-Mercaptoethanol per 10 mL of Buffer RLT prior to beginning protocol. 70% Ethanol: Make 50 mL of 70% ethanol by adding 35 mL absolute ethanol to 15 mL deionized, RNase-free water. 1×PBS: RNase-free water. Filter the solution using a 0.22 um filter.

Procedure: Removing Cells from the OptiCell Chamber (proceed one OptiCell at a time). Check the cells under a microscope to ensure that the cells are alive before isolating RNA. Remove and discard the cell culture medium. Using the OptiCell knife, cut away the top membrane exposing the cells on the lower membrane. Wash the membrane to which the cells are attached three times with 1×PBS. Pipette 600 uL of the Buffer RLT solution (containing β-Mercaptoethanol) onto the center of the membrane to which the cells are attached. Using the cell scraper, gently spread the Buffer RLT over the entire surface of the membrane, and then collect the liquid in one corner. Pipette off the entire volume of Buffer RLT and place into a QIAshredder spin column.

RNA Isolation: Centrifuge the QIAshredder spin columns at 14,000 rpm for 2 minutes. Discard the spin column but keep the collection tube and its contents. Add 600 uL of 70% ethanol to the collection tube and mix well by pipetting (the total volume now=1.2 mL). Transfer 600 uL of the cell lysate to an RNeasy mini column and centrifuge for 15 seconds at 14,000 rpm. Discard the flow through but keep the collection tube and the spin column. Transfer the remaining volume of cell lysate (~600 uL) to the spin column and repeat the centrifugation. Discard the flow through but keep the collection tube and the spin column. Add 700 uL Buffer RWI to the spin column. Centrifuge for 15 seconds at 14,000 rpm to wash the column. Discard the flow through and the collection tube. Transfer the spin column to a new 2 mL collection tube and add 500 uL Buffer RPE to the column. Centrifuge for 15 seconds at 14,000 rpm. Discard the flow through, keep the collection tube/column. Add another 500 uL Buffer RPE to the column. Centrifuge for 2 minutes at 14,000 rpm. Transfer the spin column to a 1.5 mL collection tube. Add 30 uL of RNA Storage Solution directly to the silica gel membrane and centrifuge for 1 minute at 14,000 rpm to elute the RNA. Store the final RNA at −70° C.

RNA 6000 Nano Assay. Using the Agilent 2100 Bioanalyzer and the RNA 6000 Nano Assay, analyze RNA isolated from cultured mammalian cells, lymphocytes or tissues for quality.

Reagents: RNA 6000 Nano gel matrix, RNA 6000 Nano dye concentrate, RNA 6000 Nano Marker, (all of the above reagents are contained in the RNA 6000 Nano Assay kit, Agilent), RNA 6000 ladder, RNase Zap, and RNase-free water, from Ambion.

Equipment/Other Materials: Agilent Chip Priming Station, Agilent, RNA 6000 chip, Agilent, electrode cleaners, P2, P10, P200, and P1000 Rainin Pipetman pipettes, sterile, DNase/RNase free filtered pipette tips, 1.5 mL microcentrifuge tubes, sterile, vortex, IKA vortex mixer, microcentrifuge, and heating block.

Procedure: The procedure is given in the Reagent Kit Guide, RNA 6000 Nano Assay, Edition November 2003, by Agilent Technologies. The procedures are followed as given in the Guide, with the following modifications: Preparing the Gel, pg. 17—rather than separating the filtered gel into aliquots of 65 uL each, keep the stock filtered gel in the original microcentrifuge tube and aliquot the 65 uL as needed. Loading the RNA 6000 Nano Marker, pg. 22—add 1 uL of RNase-free water (instead of RNA 6000 Nano Marker) to each sample well that will not contain sample. Not only will this conserve the amount of Marker used but also serves as a negative control to see that none of the reagents are contaminated, including the RNase-free water. Loading the Ladder and Samples, pg. 23—heat denature the samples and RNA 6000 Ladder for an additional 30 seconds (total of 2.5 minutes) at 71° C. Starting the Chip Run, pg. 26—choose the "Eukaryote Total RNA Nano" option from the assay menu.

Example 5

Affymetrix GeneChip Expression Analysis

Gene expression is analyzed using a proprietary Affymetrix Feline GeneChip®. Total RNA is reverse transcribed into cDNA. The cDNA is used to generate cRNA which is fragmented and used as probes for GeneChip hybridization. The gene chip is washed and the hybridization signal is measured with an Affymetrix laser scanner. The hybridization data is then validated and normalized for further analysis in accordance with instructions from the manufacturer.

Equipment: Eppendorf microcentrifuge, 1.5 mL DNase and RNase free/sterile microcentrifuge tubes, 50 mL DNase and RNase free/sterile disposable polypropylene tubes, P1000, P200, P20, P10 and P2 Rainin Pipetman pipettes, Filter pipette tips for P1000, P200, P20, P10 and P2 pipettes, DNase and RNase free/sterile, and Peltier Thermal Cycler PTC-200.

Procedure: follow all procedures exactly as described in GeneChip Expression Analysis Technical Manual (Affymetrix Copyright 1999-2003). Use 5 microgram of total RNA for the first strand cDNA synthesis. Use either Peltier Thermal Cycler PTC-200 or heat block for temperature control on reactions and probe denaturing. The quality control is performed using RNA NanoDrop chips with BioAnalyer 2100. Use 100 Format (Midi Array) for the feline genechip.

Example 6

Gene Expression in Felines with Chronic Kidney Disease

Studies were conducted in accordance with the previous Examples 1-5 using felines having various stages of chronic kidney disease to determine the underlying gene expression differences between felines with normal renal function and felines having minimal, mild, moderate and marked glomerulonephritis corresponding to Stages 1 through 4 as presented on Table 1. Procedures as described in the Examples of this specification were used to prepare tissue and bodily fluid samples from 15 felines having normal renal function, 4 felines having minimal glomerulonephritis, 10 felines having mild glomerulonephritis, 20 felines having moderate glomerulonephritis and 13 felines having marked glomerulonephritis, as determined by plasma creatinine levels presented in Table 2 and by clinical observation.

Based on gene expression data comparing the felines with normal renal function versus felines having glomerulonephritis, as defined in the preceding examples, the four genes listed on Table 3 were identified as meeting the selection criteria of Example 2 as potential biomarkers of chronic kidney disorders in felines. The genes include lumican (LUM), collagen alpha 1 (III) chain, variant 12 (COL3A1), Decorin (DCN), and secreted frizzled-related protein 2 (SFRP2). Analogous human synonyms and mRNA and protein accession numbers are listed on Table 3 for each gene. Each of the proteins is a secreted protein. Geometric fold change data plotted versus the stage of glomerulonephritis for each of the five genes is presented in FIGS. 1 to 4, respectively.

Figure 1B:
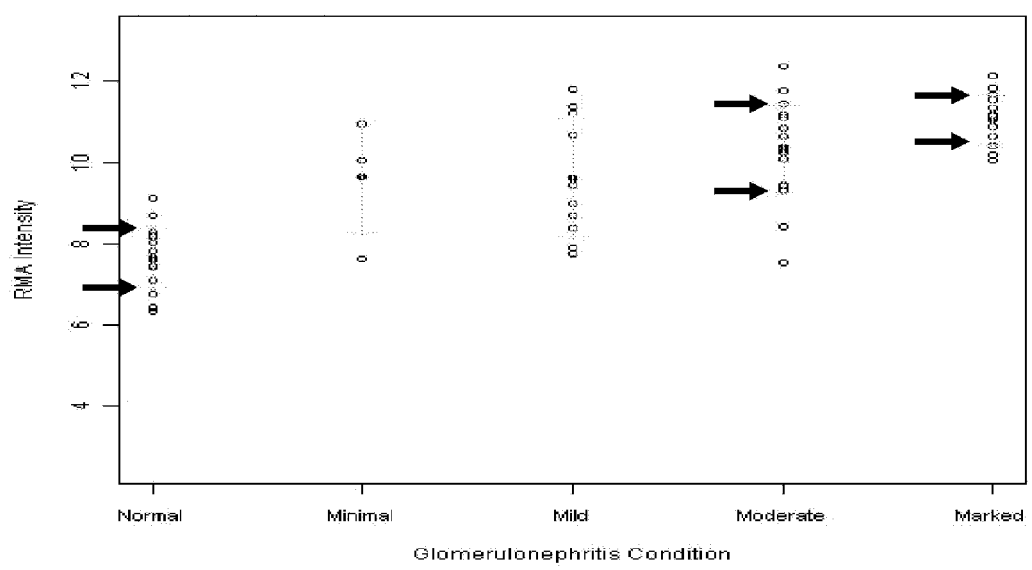
FIG. 1b is a plot of the geographic mean RMA intensity versus the stage of glomerulonephritis of a subject feline for the expression of the gene *Canis familiaris* similar to lumican precursor (keratan sulfate proteoglycan lumican) mRNA.

FIG. 1a demonstrates a geometric mean fold change of 10 in felines having marked glomerulonephritis over normal felines for the lumican gene expression product. FIG. 1b presents geometric mean RMA intensity data plotted versus the stage of glomerulonephritis for each of the tested animals.

Figure 2A:
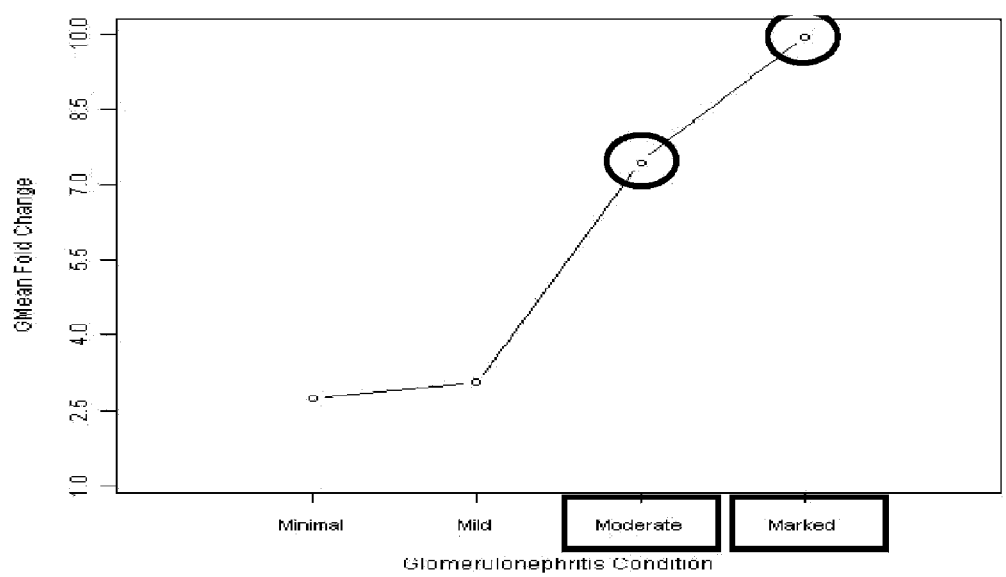
FIG. 2a is a plot of the geographic mean fold change versus the stage of glomerulonephritis of a subject feline for the expression of the gene *Equus caballus* similar to collagen alpha 1(III) mRNA.
Figure 2B:
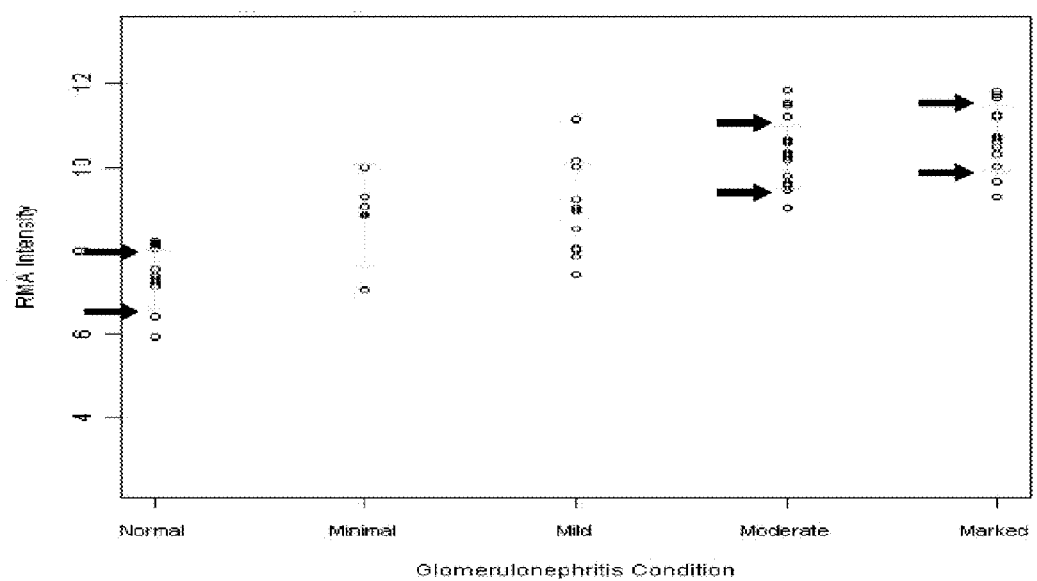
FIG. 2b is a plot of the geographic mean RMA intensity versus the stage of glomerulonephritis of a subject feline for the expression of the gene *Equus caballus* similar to collagen alpha 1 (III) mRNA.

FIG. 2a demonstrates a geometric mean fold change of 10 in felines having marked glomerulonephritis over normal felines for the COL3A1 gene expression product. FIG. 2b presents geometric mean RMA intensity data plotted versus the stage of glomerulonephritis for each of the tested animals.

Figure 3A:
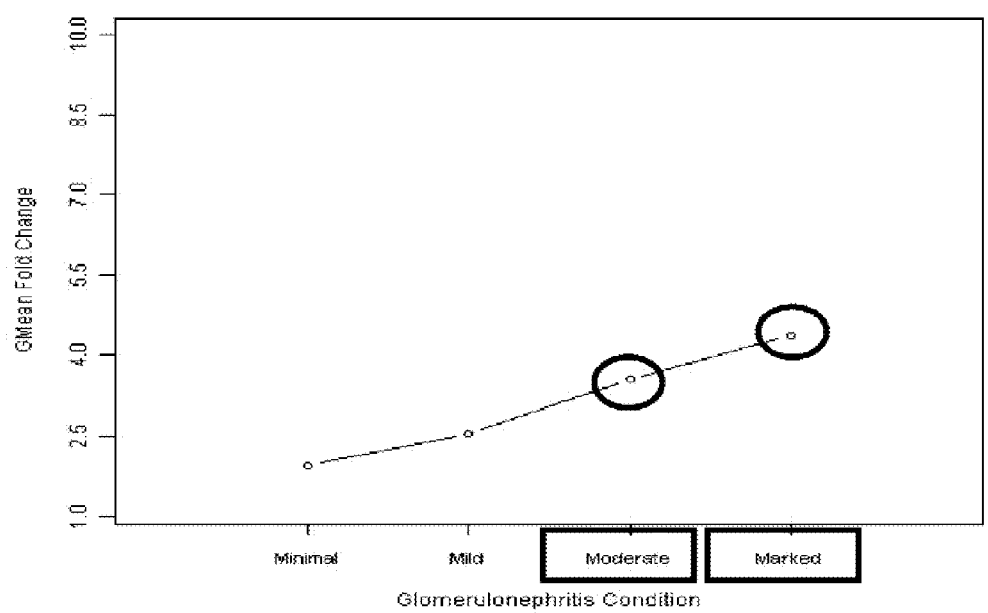
FIG. 3a is a plot of the geographic mean fold change versus the stage of glomerulonephritis of a subject feline for the expression of the feline gene *Canis lupus familiaris* decorin mRNA, complete felines.
Figure 3B:
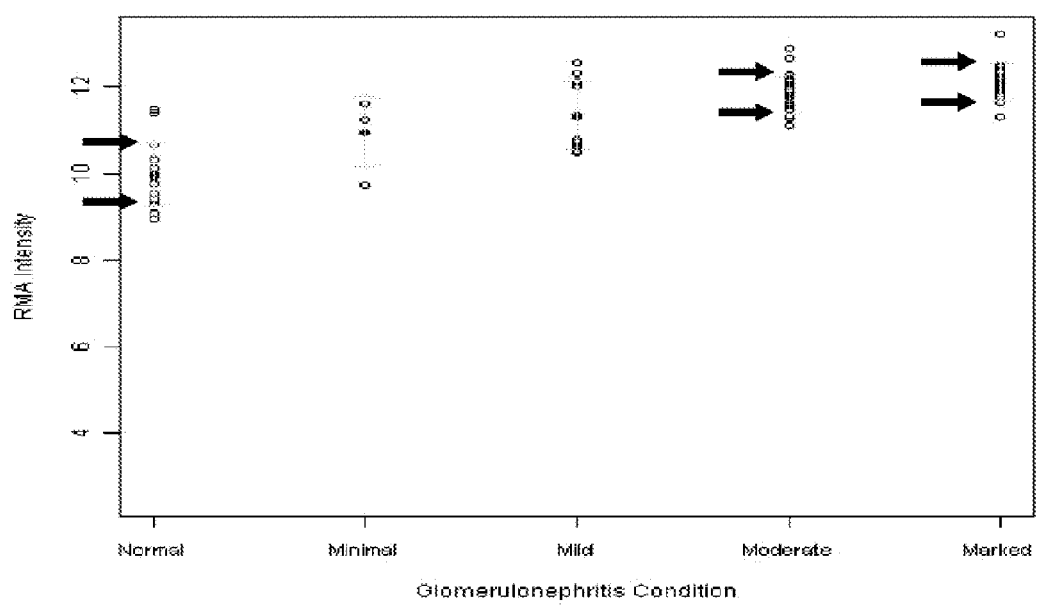
FIG. 3b is a plot of the geographic mean RMA intensity versus the stage of glomerulonephritis of a subject feline for the expression of the feline gene *Canis lupus familiaris* decorin mRNA, complete felines.

FIG. 3a demonstrates a geometric mean fold change of 4.3 in felines having marked glomerulonephritis over normal felines for the decorin gene expression product. FIG. 3b presents geometric mean RMA intensity data plotted versus the stage of glomerulonephritis for each of the tested animals.

Figure 4A:
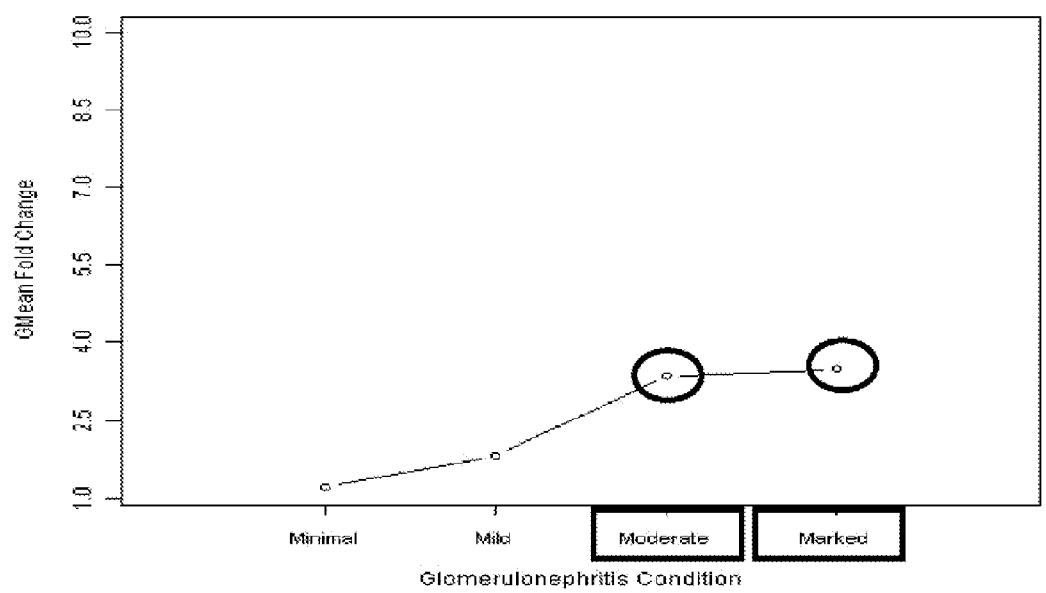
FIG. 4a is a plot of the geographic mean fold change intensity versus the stage of glomerulonephritis of a subject feline for the expression of the gene *Canis lupus familiaris* secreted frizzled-related protein 2 mRNA.
Figure 4B:
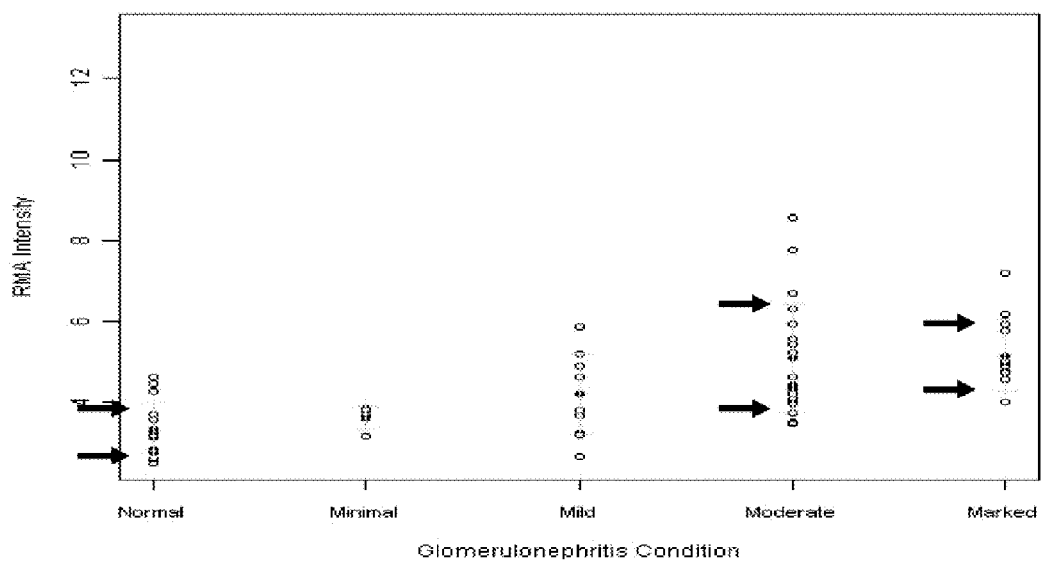
FIG. 4b is a plot of the geographic mean RMA versus the stage of glomerulonephritis of a subject feline for the expression of the gene *Canis lupus familiaris* secreted frizzled-related protein 2 mRNA.

FIG. 4a demonstrates a geometric mean fold change of 3.8 in felines having marked glomerulonephritis over normal felines for the SFRP2 gene expression product. FIG. 4b presents geometric mean RMA intensity data plotted versus the stage of glomerulonephritis for each of the tested animals.

Figure 5A:
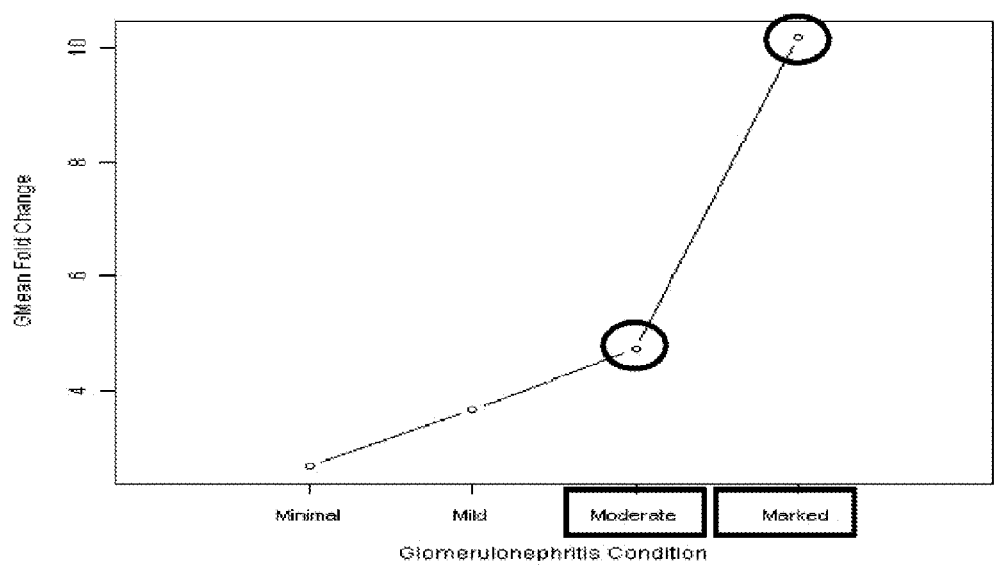
FIG. 5a is a plot of the geographic mean fold change versus the stage of glomerulonephritis of a subject feline for the expression of the gene *Canis familiaris* matrix metalloproteinase 2 mRNA.
Figure 5B:
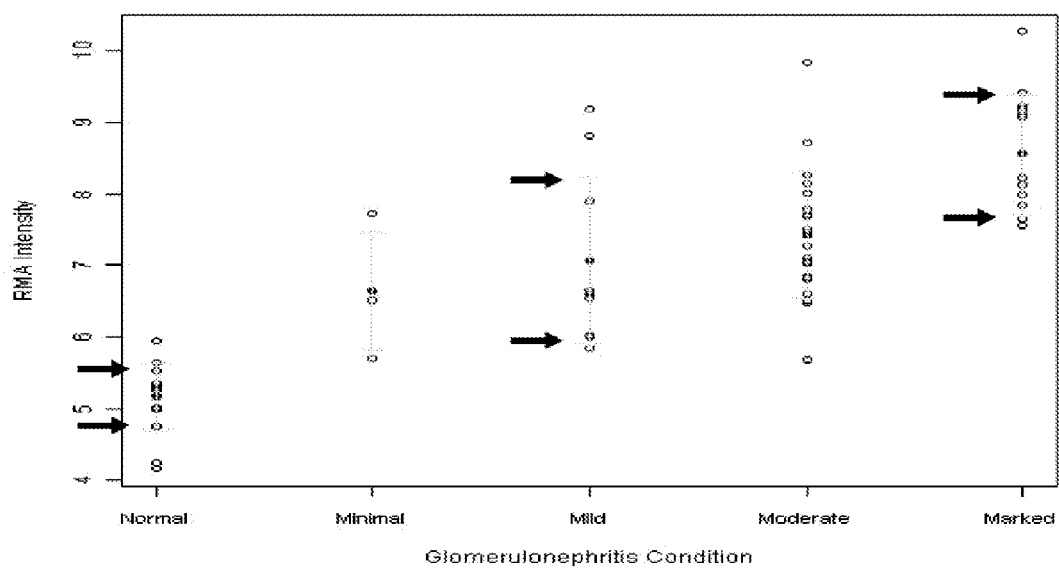
FIG. 5b is a plot of the geographic mean RMA intensity versus the stage of glomerulonephritis of a subject feline for the expression of the gene *Canis familiaris* similar to matrix metalloproteinase 2 mRNA.

FIG. 5a demonstrates a geometric mean fold change of 10.3 in felines having marked glomerulonephritis over normal felines for the matrix metalloproteinase-2 gene expression product. FIG. 5b presents geometric mean RMA intensity data plotted versus the stage of glomerulonephritis for each of the tested animals.

Figure 6A:
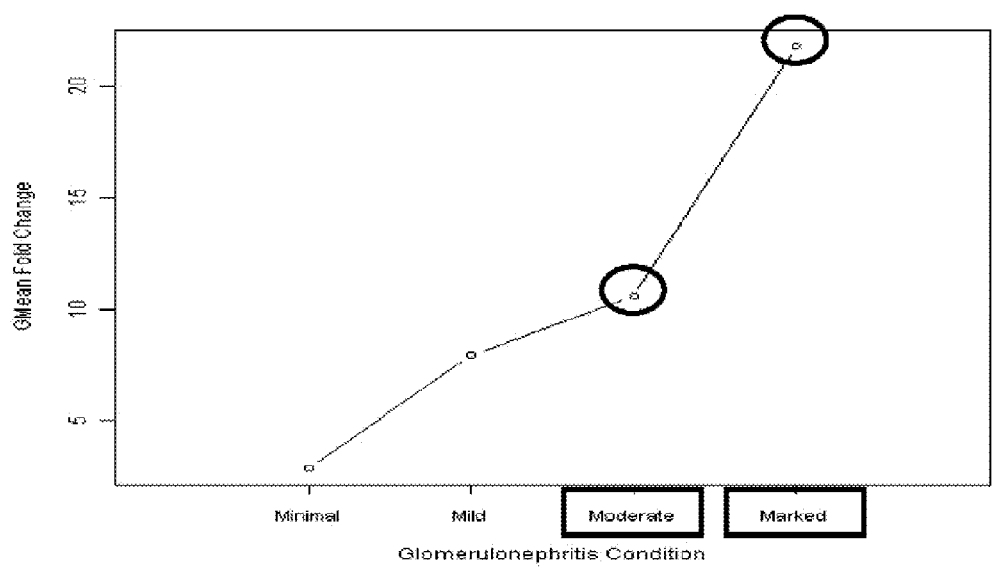
FIG. 6a is a plot of the geographic mean fold change versus the stage of glomerulonephritis of a subject feline for the expression of the gene *Felis domesticus* PUMP-1 mRNA.
Figure 6B:
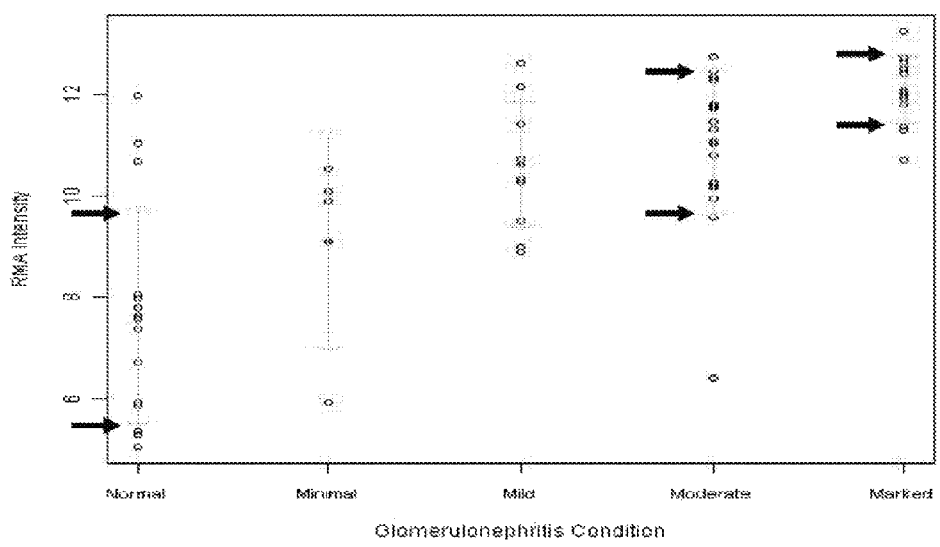
FIG. 6b is a plot of the geographic mean RMA intensity versus the stage of glomerulonephritis of a subject feline for the expression of the gene *Felis domesticus* PUMP-1 mRNA.

FIG. 6a demonstrates a geometric mean fold change of 23 in felines having marked glomerulonephritis over normal felines for the matrix metalloproteinase-7 gene expression product. FIG. 6b presents geometric mean RMA intensity data plotted versus the stage of glomerulonephritis for each of the tested animals.

Figure 7A:
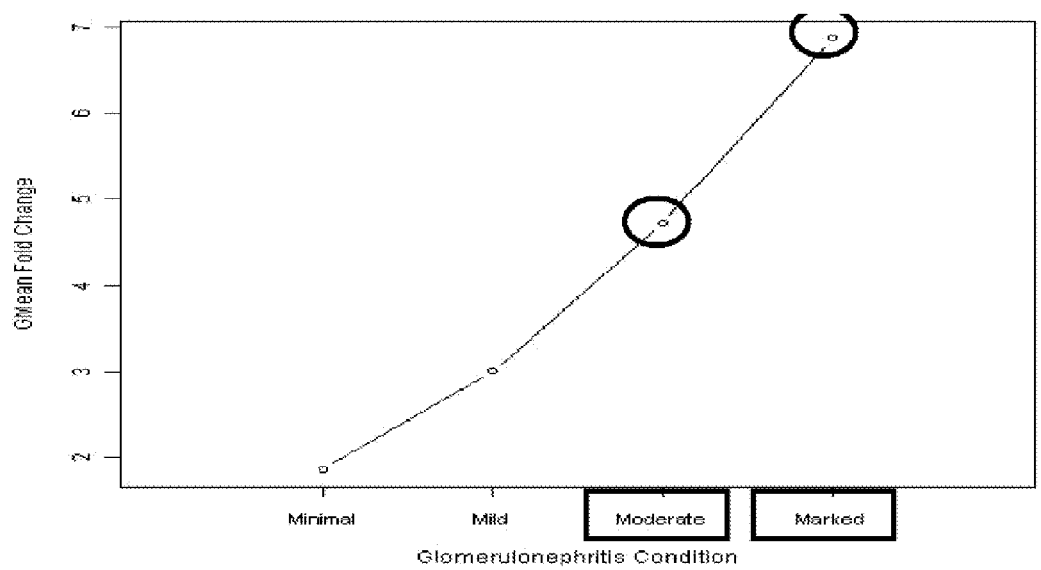
FIG. 7a is a plot of the geographic mean fold change versus the stage of glomerulonephritis of a subject feline for the expression of the gene *Mucaca mulatta* mRNA.
Figure 7B:
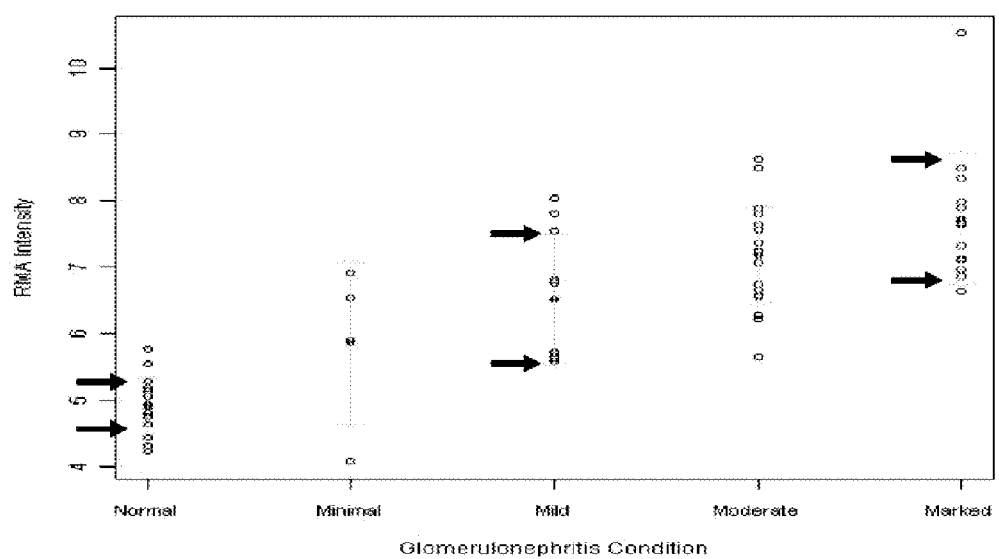
FIG. 7b is a plot of the geographic mean RMA intensity versus the stage of glomerulonephritis of a subject feline for the expression of the gene *Mucaca mulatta* mRNA.

FIG. 7a demonstrates a geometric mean fold change of 6.9 in felines having marked glomerulonephritis over normal felines for the matrix metalloproteinase-19 gene expression product. FIG. 7b presents geometric mean RMA intensity data plotted versus the stage of glomerulonephritis for each of the tested animals.

Figure 8A:
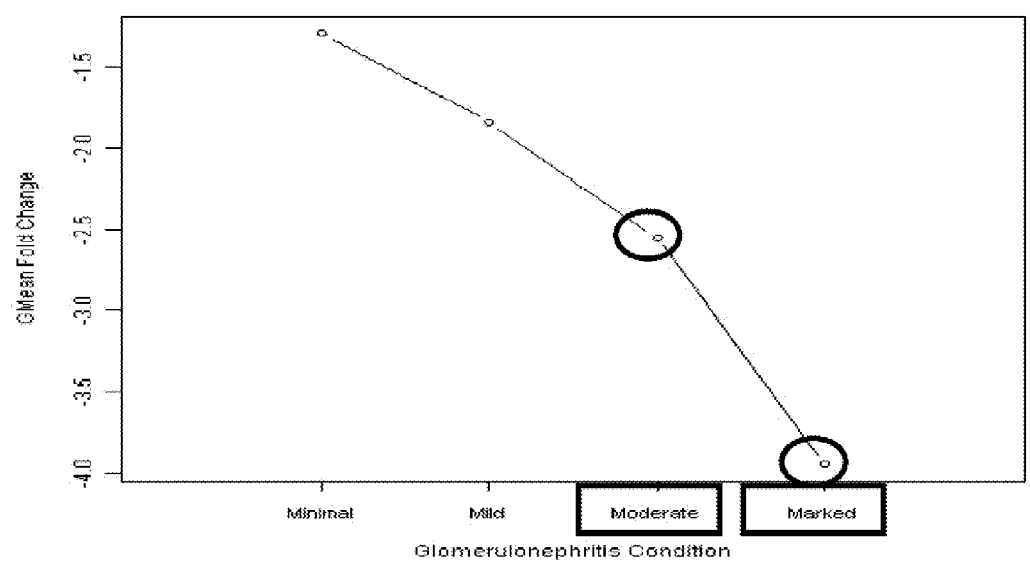
FIG. 8a is a plot of the geographic mean fold change versus the stage of glomerulonephritis of a subject feline for the expression of the feline gene similar to *Canis familiaris* retinol-biding protein 5, cellular.
Figure 8B:
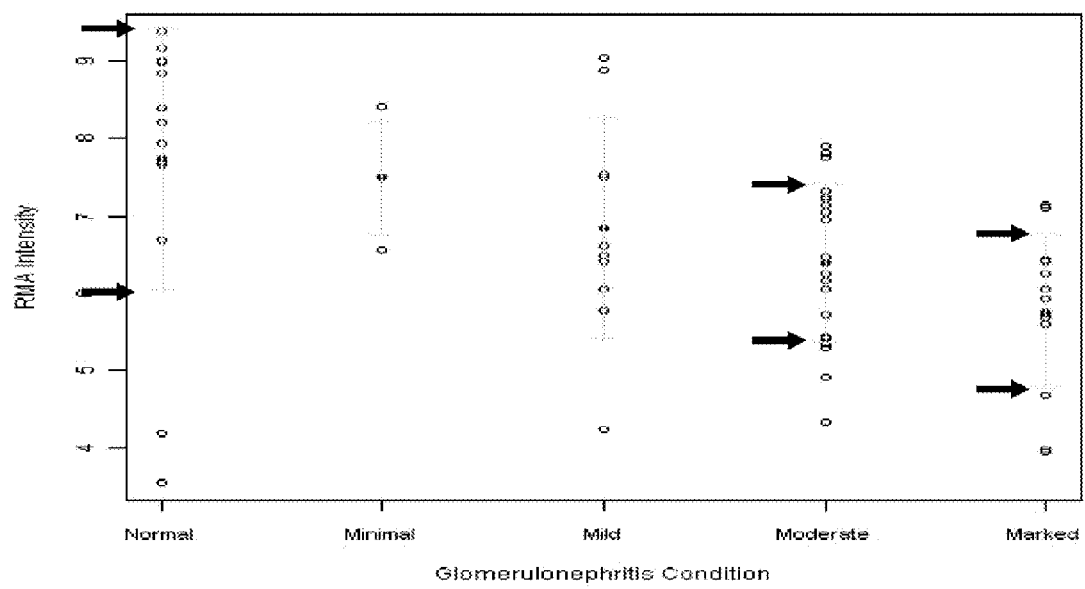
FIG. 8b is a plot of the geographic mean RMA intensity versus the stage of glomerulonephritis of a subject feline for the expression of the gene similar to *Canis familiaris* retinol-biding protein 5, cellular.

FIG. 8a demonstrates a geometric mean fold change of 3.9 downregulation in felines having marked glomerulonephritis over normal felines for the retinol-binding protein 5 gene expression product. FIG. 8b presents geometric mean RMA intensity data plotted versus the stage of glomerulonephritis for each of the tested animals.

Although any compositions, methods, articles of manufacture, or other means or materials similar or equivalent to those described herein can be used in the practice of the present invention, the preferred compositions, methods, articles of manufacture, or other means or materials are described herein.

TABLE 3

List of Biomarkers

| Gene | Symbol Feline | Human Synonyms | Homolog Synonym | Gene Description | mRNA | Protein |
|---|---|---|---|---|---|---|
| Lumican | LUM | LDC; SLRR2D | Canine LUM | Similar to Lumican precursor | XM_539716.2 Gene ID: 482599 | XP_539716.1 |
| Collagen alpha 1 (III) chain, variant 12 | COL3A1 | EDS4A; FLJ34534 | Equine COL3A1 | Collagen, type III, alpha 1 (Ehlers Danlos syndrome IV, autosomal dominant) | XM_001917620.1 Gene ID: 100034123 | XP_001917655 |
| Decorin | DCN | CSCD; DSPG2; PG40; PGII; PGS2; SLRR1B | Canine DCN | Decorin | NM_001003228.1 Gene ID: 403904 | NP_001003228.1 |
| SFRP2 | SFRP2 | FRP-2; SARP1; SDF-5 | Canine Sfrp2 | Secreted frizzled-related protein 2 | NM_001002987.1 Gene ID: 475471 | NP_001002987.1 |

TABLE 4

List of Biomarkers

| Gene | Symbol Feline | Human Synonyms | Homolog Synonym | Gene Description | mRNA | Protein |
|---|---|---|---|---|---|---|
| Retinol Binding Protein 5 | Rbp5 | Rbp-5 | Canine Rbp5 | retinol binding protein 5, cellular | XM_848184.1 LOC477706 | XP_853277.1 |
| MMP-2 | MMP2 | MMP2 | Canine | matrix metalloproteinase 2 (gelatinase A, 72 kDa gelatinase, 92 kDa type IV collagenase) | XM_535300.2 Gene ID: 4037333 | XP_535300.2 |
| MMP-7 | MMP7 | MMP7 PUMP-1 | Feline PUMP-1 | matrix metalloproteinase 7 | FDU04444 GeneBank U04444.1 | AAA18222.1 |
| MMP-19 | MMP19 | MMP19 | *Macaca Mulatta* MMP19 | matrix metalloproteinase 19 | XM_001111542.1 | XP_001111542.1 |

What is claimed is:

1. A method of diagnosing the existence of a kidney disorder in a feline comprising measuring the level of expression of one or more biomarkers selected from the group consisting of lumican; collagen alpha 1(III) chain, variant 12; decorin; secreted frizzled-related protein 2; retinol binding protein 5; MMP-2; MMP-7; and MMP-19, in a biological sample from the feline,
comparing the level of expression of the one or more biomarkers in the biological sample from the feline to a control value, and
diagnosing the existence of the kidney disorder in the feline, wherein differences in expression of the one or more biomarkers in the sample relative to the control value for expression in a sample from a normal animal indicate the existence of a kidney disorder,
wherein the level of expression of the one or more biomarkers is determined by measuring gene expression of the one or more biomarkers using a DNA microarray comprising one or more oligonucleotides complementary to mRNA or cDNA corresponding to the one or more biomarkers to be measured, and
wherein the oligonucleotides in the DNA microarray comprise one or more probes comprising sequences selected from one or more of SEQ ID NOS. 1-8.

2. The method of claim 1 comprising detecting expression levels of secreted frizzled-related protein-2 (SFRP2) and/or retinol binding protein 5 (rbp5) and, optionally, expression levels of at least one gene selected from the group consisting of: lumican (LUM); decorin (DCN); collagen alpha 1 (III) chain, variant 12 (COL3A1)); matrix metalloproteinase-2 (MMP2); matrix metalloproteinase-7 (MMPI, PUMP-1); and matrix metalloproteinase-19 (MMP19).

3. The method of claim 1 wherein the step of measuring gene expression of one or more biomarkers comprises (i) isolating RNA from the tissue sample, (ii) reverse transcribing the RNA to obtain the corresponding cDNA, (iii) isolating and fragmenting the cDNA thus obtained, (iv) contacting the cDNA fragments with a DNA microarray comprising one or more oligonucleotides complementary to cDNA corresponding to the one or more biomarkers to be measured, and (v) detecting hybridization between the cDNA fragments and the one or more oligonucleotides in the DNA microarray.

4. The method of claim 1 wherein the biological sample is blood or a sample of renal tissue.

5. The method of claim 1 comprising detecting expression levels of secreted frizzled-related protein-2 (SFRP2) and/or retinol binding protein 5 (rbp5).

6. The method of claim 1 wherein the feline has essentially normal kidney function, as measured by one or more of the following: normal glomerular filtration rate, creatinine clearance rate, urinary protein levels, serum creatinine levels, urinary creatinine levels, blood urea nitrogen (BUN) levels, radioisotope metabolic labeling, soft tissue imaging, including sonography, magnetic resonance imaging and/or computed tomography.

7. The method of claim 1 wherein the kidney disorder is a disorder characterized by an abnormal loss of renal function, renal failure, reduced glomerular filtration rate or glomerulonephritis.

8. The method of claim 1 wherein the kidney disorder is glomerulonephritis.

9. The method of claim 1 wherein the existence of a kidney disorder is indicated by a significant difference in expression of one or more of the following relative to control expression values wherein a "significant difference" in the case of increased expression is an increase of at least twofold and in the case of decreased expression is a decrease of at least 50%:
  a. Lumican expression increased;
  b. Collagen alpha 1(III) chain, variant 12 expression increased;
  c. Decorin expression increased;
  d. Secreted frizzled-related protein 2 expression increased;
  e. Retinol Binding Protein 5 expression decreased;
  f. MMP-2 expression increased;
  g. MMP-7 expression increased; and/or
  h. MMP-19 expression increased.

10. A method of treating, ameliorating, or delaying the progression of a kidney disorder characterized by an abnormal loss of renal function, renal failure, reduced glomerular filtration rate or glomerulonephritis in a feline, comprising diagnosing the existence of a kidney disorder by the method of claim 1 and managing the disorder by a kidney protective diet and/or medication.

11. The method of claim 10 wherein the step of managing the disorder comprises providing a kidney protective diet as substantially the sole diet to the feline.

12. The method of claim 10 wherein the kidney protective diet comprises one or more of the following modifications relative to a standard feline diet:
  a. Reduced phosphorus
  b. Reduced levels of protein
  c. Reduced sodium
  d. Increased levels of omega-3 fatty acids
  e. Increased levels of B-complex vitamins
  f. Increased antioxidants.

13. The method of claim 10 wherein the kidney protective diet comprises from about 18% to about 40% protein, from about 0.2% to about 0.85% phosphorus, and from about 0.04% to about 0.35% sodium, on a dry matter basis.

14. The method according to claim 12 comprising detecting expression levels of secreted frizzled-related protein-2 (SFRP2) and/or retinol binding protein 5 (rbp5).

* * * * *

```
                        SEQUENCE LISTING

<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
atcaccgcac gagttcttca aataa                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
aggtgctgag ggtcttgact accac                                          25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
atttcaagcg tttcagtggg ctgca                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
atacatccag gttgtctacc ttcat                                          25
```

```
<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
atgccagtcc tgtgaatgtt ccacg                                              25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
agacctacat ctttgctgga gacaa                                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
atcgcccggc gagagcttga aattc                                              25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
atgcagctct ctattggcct ttcaa                                              25

<210> SEQ ID NO 9
<211> LENGTH: 534
<212> TYPE: DNA
<213> ORGANISM: Felis domesticus

<400> SEQUENCE: 9
aaccccaccc agatcatgta gaaatgttta aactaataaa atcatgaata tttttatgaa         60 gttttaaat agctcgcttt agtgttgaat agctacaacc gtgacttggg tctgatattt        120
ttgttttcct gtttggtttg ggtcagctgt ttttcacttt ctgctaaggt tgccataacg       180
tgcaaatagc ttcattttc aatgtggccc aaactgttgt gggtcacaaa cctcgttgag        240
ataaagctgg ctgttatctc aacatgtctc ggctccagcc tgagactgag agcctaagtc       300
ttcaaattca cttgtacttt cacccctca ttgggaactt acagcagtcg catgttatta       360
cacttccacg tagagtactt ccatctctaa agagcacatt aaccatcacc gcacgagttc       420
ttcaaataaa gggccaacag acagatttca taactgacct gcgtactttta agctttgttt     480 caaacacttt tctatctaat tctgcaaact caaccattgt agcttacccg ctaa            534

<210> SEQ ID NO 10
```

```
<211> LENGTH: 331
<212> TYPE: DNA
<213> ORGANISM: Felis domesticus

<400> SEQUENCE: 10
agtcagttcc agatacagcg tctctccctc cagccagtgt ctccagcctc ggttggggac      60
ctcccctttc tgcacacata ctagctgctc ctcctcccag gttactatgg tctggcattt     120
tcgtccatcc acgatcctta gatcttcttc aaactcaact cccacatcga attccagaat     180
gtagttgcgg aaggtgctga gggtcttgac taccacgtgg ttgccctgat ggtcaatctc     240
cttgtctggc ttgaccagca gcgctatctt ccgcaaggcc atgcggaatg tttagggctt     300
gcaagtaagg gtttcatgtt cttctgccaa a                                    331

<210> SEQ ID NO 11
<211> LENGTH: 411
<212> TYPE: DNA
<213> ORGANISM: Felis domesticus

<400> SEQUENCE: 11
tggatctcca gcttacgcac aacaagataa cgaagcttgg ctccttcgat ggactggtaa      60
acctgacctt cgtccacctc caacacaatc aactgaaaga ggatgctgtt tcagctgctt     120
ttaaaggtct taagtccctc gaataccttg acttgagctt caaccagatg gccaaactgc     180
cctctggtct cccagcatct cttctaactc tctacttgga caacaataag atcagcaaca     240
tccctgatga gtatttcaag cgtttcagtg ggctgcagta tctacgttta tctcacaatg     300
aactggctga tagtggagta cctggaaatt cttttaatgt atcatccctg cttgagctgg     360
atctctccta taataagctt aaaaacatac cgactgtcaa cgagaacctt g              411

<210> SEQ ID NO 12
<211> LENGTH: 458
<212> TYPE: DNA
<213> ORGANISM: Felis domesticus

<400> SEQUENCE: 12
atgaagaagc tgtcctacat ccgcattgcc gacaccaata taaccaccat cccgcaaggt      60
cttcctcctt cccttactga attacatctt gaaggcaaca aaatctccaa agttgatgca     120
gctagcctga aaggactgaa taatttggct aagttgggac tgagttttaa cagcatctct     180
gctattgaca atggcactct ggccaacact cctcatttga gggagcttca cttggacaac     240
aataagctta tcagagtacc tggtgggctg gcggagcaca atacatcca ggttgtctac      300
cttcataaca acaatatctc tgcagtcggg tctaacgact tctgcccact gggatacaac     360
accaaaaagg gcttcttaat caggtgtgaa ccctttcag caacccatcc catactggga      420
gaatccaccc tccaccttcc atgggtctat ttgcgttc                             458

<210> SEQ ID NO 13
<211> LENGTH: 535
<212> TYPE: DNA
<213> ORGANISM: Felis domesticus

<400> SEQUENCE: 13
agacctgaag ttctgccatc ctgaactcca gagtggagaa tattggattg atcctaacca      60
aggctgcaag ttggatgcta ttaaagtatt ctgtaatatg gaaactgggg aaacatgcat     120
aaatgccagt cctgtgaatg ttccacgtaa gaactggtgg atagattctg gtgctgagaa     180
gaaacatgtt tggtttggag aaaccatgga tggtggtttt cagtttagct atggcaatcc     240
```

```
tgaccttcct gaagatgtcc tcgatgtcca gctggcattc ctccgacttc tctccagccg    300
ggcctcccaa acatcacgt atcactgcaa gaatagcatt gcatacatgg atcaggccag     360
tgggaatgta agaaagccc tgaggctgat gggttcaatg aaggtgaatt ccaggctgaa     420
gggaatagca aattcacata cacagttctg gaggatggtt gcactaaaca cactggggga    480
atggggcaaa acagtcttca aatatcgaac acgcaaggcc gtgagattac ctatt         535
```

<210> SEQ ID NO 14
<211> LENGTH: 511
<212> TYPE: DNA
<213> ORGANISM: Felis domesticus

<400> SEQUENCE: 14

```
gaatactggg tctactcagc cagcaccctg gagcgagggt accccaagcc gctgaccagc     60
ctggggctgc ccccgacgt ccagcgggta gatgctgcgt ttaactggag caagaacagg    120
aagacctaca tctttgctgg agacaagttc tggaggtaca atgaagtaaa gaaaaagatg    180
gaccctggct tccccaagct catcgcggat gcctggaacg ccatcccga taacctggac    240 gccgtggtcg acctgcaggg cggtggtcac agctacttct tcaagggcgc gtattacctg    300
aagttggaga accagagtct gaagagcgtg aaatttggaa gcatcaaatc cgactggctg    360
ggctgctgag ccgcctctgg ctcctccagg ccccgcgcgt ccatgtcttc tgcaaaacca    420
ggccctgagc gccagggaag gacccggaag gggcctggca gcctttcagc tctgtagtta    480
atcagcgttc tcaccctacc tggtaattta a                                    511
```

<210> SEQ ID NO 15
<211> LENGTH: 527
<212> TYPE: DNA
<213> ORGANISM: Felis domesticus

<400> SEQUENCE: 15

```
tgaatgaacg tgtgctctcc ccgaagttcc tacttctttc ttgatttact tctctttcca     60
tacaattcct ggatttctct gatatcgccc ggcgagagct tgaaattctc agagtccctg    120
gctccgtagg tgggtacat gacagagtcg ggatcagacg aatgtctcag gcccagagaa    180
tggccaagtt catgggttgc aacagccagg aagttaattc ctagacccct gccgtcggcc    240
cagcgctcgt cctcatcgaa gtgggcgtct cctcccaggc ccggcccagg ttcgtaggca    300
tgggccagtg tgcctcctgg tccgtcaaat gggtagaagt ccccgtgagc tcctcttgca    360
aagccaatca cgatatcggg aattcccagc acaactctcc tgaaggatag tgggatctct    420 tgctccaca tattcaaggc ctttgccact aaatgatcca ctgtgacacg tggtaagtct    480
cgagtgtatg atatgatcct gtaggtgacc actttggaaa tcccctt                 527
```

<210> SEQ ID NO 16
<211> LENGTH: 511
<212> TYPE: DNA
<213> ORGANISM: Felis domesticus

<400> SEQUENCE: 16

```
gaaacctaga tgctgctgtc tactctcctc gaacacaatg gattcacttc tttaagggag     60
acaaggtgtg gcgctatatt aatttcaaga tgtctcctgg cttcccaag aagctgaata   120 gggtagaccc ccacctggat gcagctctct attggccttt caataaaaag gtgttcctct    180
ttaagggctc cgggtactgg cagtgggacg agctggcccg aactgacttc agccactacc    240
```

```
ctaaaccaat caagggattg tttacaggag tgccagacca gccctctgct gctatgggtt    300
ggcgggatgg ccatgtctac ttcttcaagg gtaaacagta ctggcgcctc aaccagcagc    360
ttcgagtaga gaaaggctat cccagagata ctgcccacaa ttggatgcac tgtcatcccc    420
agacctcaaa caatactcca ttgggtgggg acaccactcc ttcagggact gacaactcaa    480
ccataggaac aaactttgga taccttcct c                                   511
```